United States Patent
Srinivasan et al.

(10) Patent No.: US 10,913,762 B2
(45) Date of Patent: Feb. 9, 2021

(54) PROCESS FOR THE PREPARATION OF D-GLUCITOL, 1,5-ANHYDRO-1-C-[4-CHLORO-3-[[4-[[(3S)-TETRAHYDRO-3-FURANYL]OXY]PHENYL]METHYL]PHENYL]-, (1S) AND ITS CRYSTALLINE FORMS THEREOF

(71) Applicant: MSN LABORATORIES PRIVATE LIMITED, Telangana (IN)

(72) Inventors: Thirumalai Rajan Srinivasan, Telangana (IN); Eswaraiah Sajja, Telangana (IN); Venkata Panakala Rao Gogulapati, Telangana (IN); Rajeshwar Reddy Sagyam, Telangana (IN); Rajesham Boge, Telangana (IN); Mohammad Rafee Shaik, Telangana (IN)

(73) Assignee: MSN LABORATORIES PRIVATE LIMITED, Telangana (IN)

( * ) Notice: Subject to any disclaimer, the term of this patent is extended or adjusted under 35 U.S.C. 154(b) by 39 days.

(21) Appl. No.: 16/073,714

(22) PCT Filed: Jan. 27, 2017

(86) PCT No.: PCT/IN2017/000021
§ 371 (c)(1),
(2) Date: Jul. 27, 2018

(87) PCT Pub. No.: WO2017/130217
PCT Pub. Date: Aug. 3, 2017

(65) Prior Publication Data
US 2019/0040094 A1 Feb. 7, 2019

(30) Foreign Application Priority Data
Jan. 27, 2016 (IN) .............................. 201641002822

(51) Int. Cl.
| | | |
|---|---|---|
| *C07H 7/04* | (2006.01) | |
| *C07H 1/06* | (2006.01) | |
| *B01D 9/00* | (2006.01) | |
| *C07D 309/10* | (2006.01) | |
| *C07D 307/20* | (2006.01) | |
| *C07D 407/10* | (2006.01) | |
| *A61K 31/7048* | (2006.01) | |

(52) U.S. Cl.
CPC .............. *C07H 7/04* (2013.01); *B01D 9/0054* (2013.01); *B01D 9/0063* (2013.01); *C07D 307/20* (2013.01); *C07D 309/10* (2013.01); *C07D 407/10* (2013.01); *C07H 1/06* (2013.01); *A61K 31/7048* (2013.01)

(58) Field of Classification Search
CPC ...... B01D 9/0068; B01D 9/0054; C07H 1/06; C07H 7/04; C07D 309/10; C07D 307/20; C07D 407/10; A61K 31/7048
USPC .......................................................... 536/127
See application file for complete search history.

(56) References Cited

U.S. PATENT DOCUMENTS 7,579,449 B2 * 8/2009 Eckhardt ................ C07H 15/26
536/1.11

FOREIGN PATENT DOCUMENTS

| CN | 104788438 | 7/2015 | |
|---|---|---|---|
| WO | WO 2011/039107 A1 * | 4/2011 | ........... C07H 15/203 |
| WO | WO 2011039107 | 4/2011 | |
| WO | WO 2015/101916 A1 * | 7/2015 | ............. C07H 23/00 |
| WO | WO 2015101916 | 7/2015 | |
| WO | WO 2015132803 | 9/2015 | |

OTHER PUBLICATIONS

Node et al, Chemistry Letters, 1979, 8(1), pp. 97-98.*
Xu et al, Journal of Medicinal Chemistry, 2014, 57, 1236-1251.*
Smith et al, March's Advanced Organic Chemistry, Wiley-Interscience, 6th Ed., 2007, pp. 496-497.*
Greene et al, Protective Groups in Organic Synthesis, second Edn., John Wiley, 1991, pp. 88-90.*
International Search Report issued in International patent application No. PCT/IN2017/000 21, dated Jun. 23, 2017.

* cited by examiner

*Primary Examiner* — Ganapathy Krishnan
(74) *Attorney, Agent, or Firm* — IP Pundit LLC

(57) ABSTRACT

The present invention relates to process for the preparation of D-glucitol, 1,5-anhydro-1-C-[4-chloro-3-[[4-[[(3S)-tetrahydro-3-furanyl]oxy]phenyl] methyl]phenyl]-, (1S) formula-1 and its crystalline forms thereof.

(Formula-1)

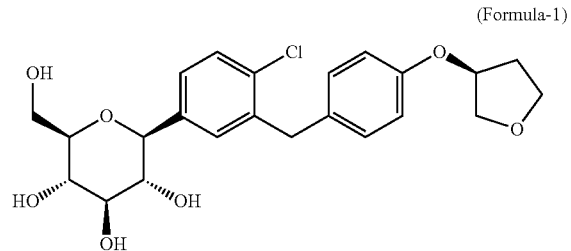

17 Claims, 4 Drawing Sheets

2-Theta-Scale

2-Theta-Scale

2-Theta-Scale

2-Theta-Scale

2-Theta-Scale

2-Theta-Scale

PROCESS FOR THE PREPARATION OF D-GLUCITOL, 1,5-ANHYDRO-1-C-[4- CHLORO-3-[[4-[[(3S)-TETRAHYDRO-3-FURANYL]OXY]PHENYL] METHYL] PHENYL]-, (1S) AND ITS CRYSTALLINE FORMS THEREOF

RELATED APPLICATIONS

This patent application is a national phase application under 35 U.S.C. § 371 of International Application No. PCT/IN2017/000021, filed on Jan. 27, 2017, which claims priority to Indian patent application number 201641002822 filed on Jan. 27, 2016 and 201641022864 filed on Jun. 4, 2016; the disclosures of which are incorporated herein by reference in their entirety.

FIELD OF THE INVENTION

The present invention is pertains to a process for the preparation of D-glucitol, 1,5-anhydro-1-C-[4-chloro-3-[[4-[[(3S)-tetrahydro-3-furanyl]oxy]phenyl]methyl] phenyl]-, (1S), which is represented by the following formula-1

(Formula-1)

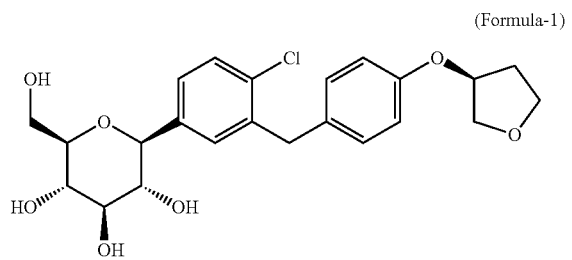 [SMILES: OC[C@H]1O[C@@H](c2ccc(Cl)c(Cc3ccc(O[C@H]4CCOC4)cc3)c2)[C@H](O)[C@@H](O)[C@@H]1O]

BACKGROUND OF THE INVENTION

D-glucitol, 1,5-anhydro-1-C-[4-chloro-3-[[4-[[(3S)-tetrahydro-3-furanyl]oxy]phenyl]methyl] phenyl]-, (1S) also known as "Empagliflozin" is sodium-glucose co-transporter 2 (SGLT2) and this drug product indicated as an adjunct to diet and exercise to improve glycemic control in adults with type 2 diabetes mellitus. It is marketed by Boehringer under the trade name Jardiance® and it is available in 10 mg and 25 mg strengths as tablet dosage forms.

U.S. Pat. No. 7,579,449 first discloses Empagliflozin product and also a process for the preparation thereof comprising 4-bromo-1-chloro-2-(4-methoxybenzyl)-benzene reacted with tribromoborane in presence of dichloromethane to produce 4-(5-bromo-2-chloro-benzyl)-phenol which is reacted with t-butyl dimethyl silyl chloride in dichloromethane in presence of triethylamine and dimethylaminopyridine to get [4-(5-bromo-2-chloro-benzyl)-phenoxy]-tert-butyldimethyl-silane which is further reacted with n-BuLi in tetrahydrofuran followed by condensation with 2,3,4,6-tetrakis-O-(trimethylsilyl)-D-glucopyranone. The resulting solution is reacted with MsOH in MeOH followed by reduction with triethylsilylhydride and boron trifluoride etherate and acylated with acetic anhydride/pyridine in dichloromethane followed by treating with KOH in MeOH to produce pentahydroxy intermediate. This pentahydroxy intermediate is reacted with tetrahydrofuran-3-yl (S)-toluene-4-sulphonate to produce the compound of formula-1.

The process is shown as below:

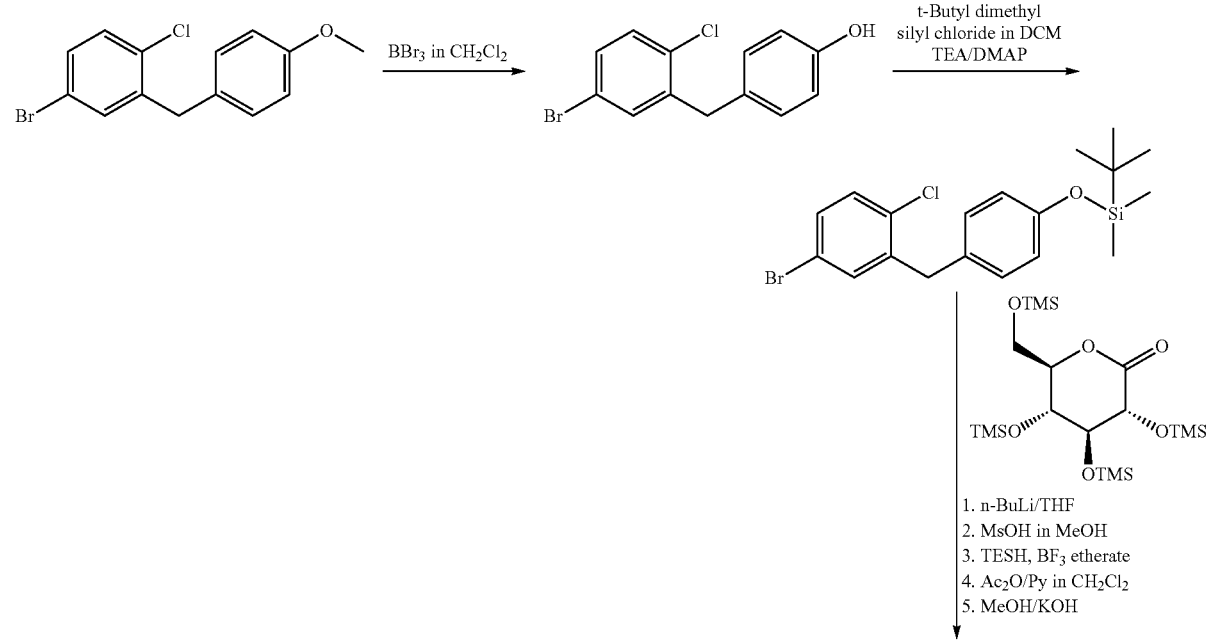

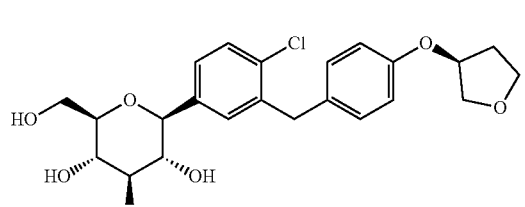

Formula-1

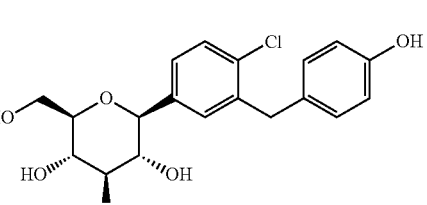

(Pentahydroxy intermediate)

Handling of tetrahydrofuran-3-yl (S)-toluene-4-sulphonate intermediate compound is very difficult in the synthesis of Empagliflozin as it mostly exist as unstable residue and accordingly reactions become challenging in the synthesis of Empagliflozin. Hence, this process is not suitable for industrial scale synthesis of Empagliflozin.

The above prior art process also produces very low yield of Empagliflozin due to reacting of pentahydroxy intermediate with tetrahydrofuran-3-yl (S)-toluene-4-sulphonate and also involves the use of hazardous $BBr_3$ as it reacts violently and decomposes to toxic compounds when on contact with moisture.

U.S. Pat. No. 7,772,191 discloses a process for the preparation of D-glucitol, 1,5-anhydro-1-C-[4-chloro-3-[[4-[[(3S)-tetrahydro-3-furanyl]oxy]phenyl] methyl] phenyl]-, (1S) of formula-1. The process is as follows:

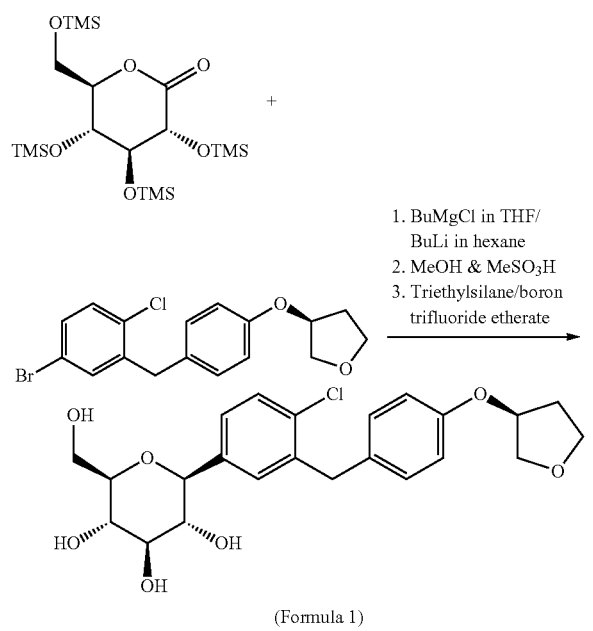

(Formula 1)

The above prior art process involves the use of BuMgCl which is extremely flammable and will cause for flash fire or ignite explosively. Hence, the handling of BuMgCl is very dangerous and will not be suitable for industrial scale preparations.

In view of the foregoing, there is still remains an alternate and improved process for the preparation of Empagliflozin of formula-1 with high chemical and enantiomerical purity and also applicable for multi-kilogram production. The process of the present invention is inexpensive, environmental-friendly having straight forward workups, rendering it amenable to the large-scale production of D-glucitol, 1,5-anhydro-1-C-[4-chloro-3-[[4-[[(3S)-tetrahydro-3-furanyl] oxy]phenyl] methyl] phenyl]-, (1S) of formula-1 with high yield.

BRIEF DESCRIPTION OF THE INVENTION

The first aspect of the present invention is to provide process for the preparation of D-glucitol, 1,5-anhydro-1-C-[4-chloro-3-[[4-[[(3S)-tetrahydro-3-furanyl]oxy]phenyl] methyl] phenyl]-, (1S) compound of formula-1.

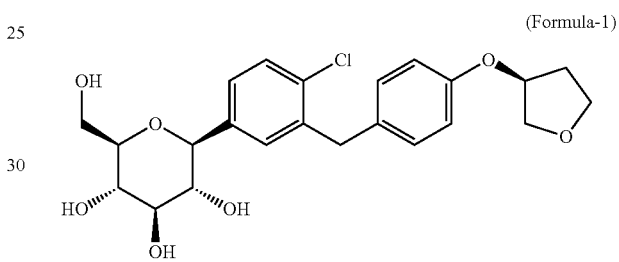

(Formula-1)

The second aspect of the present invention is to provide a process for the preparation of the compound of general formula-8.

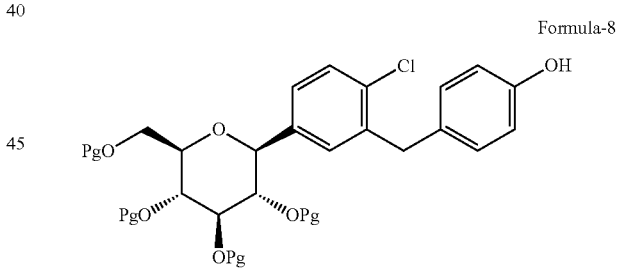

Formula-8 wherein, Pg is a protecting group which is defined hereinafter.

The third aspect of the present invention is to provide an improved process for the preparation of the compound of general formula-10.

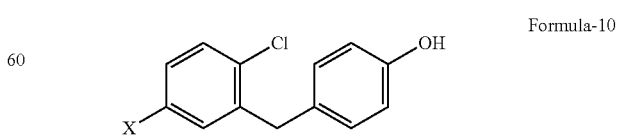

Formula-10 wherein, X is defined hereinafter.

The fourth aspect of the present invention is to provide the compound of general formula-11.

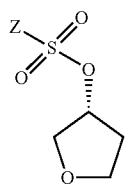

Formula-11 wherein, Z is defined hereinafter.

The fifth aspect of the present invention is to provide a process for the preparation of the compound of formula-11.

The sixth aspect of the present invention is to provide novel crystalline form (herein after designated as "form-M") of Empagliflozin and its process for preparation thereof.

The seventh aspect of the present invention is to provide crystalline Form-I of Empagliflozin-L-proline and its process for preparation thereof.

The eighth aspect of the present invention is to provide crystalline Form-II of Empagliflozin-L-proline and its process for preparation thereof.

The ninth aspect of the present invention is to provide crystalline Form-III of Empagliflozin-L-proline and its process for preparation thereof.

The tenth aspect of the present invention is to provide crystalline Form-IV of Empagliflozin L-proline and its process for preparation thereof.

The eleventh aspect of the present invention is to provide crystalline N-methyl-2-pyrrolidone solvate of Empagliflozin and its process for preparation thereof.

DETAILED DESCRIPTION OF THE INVENTION

Figure 1:
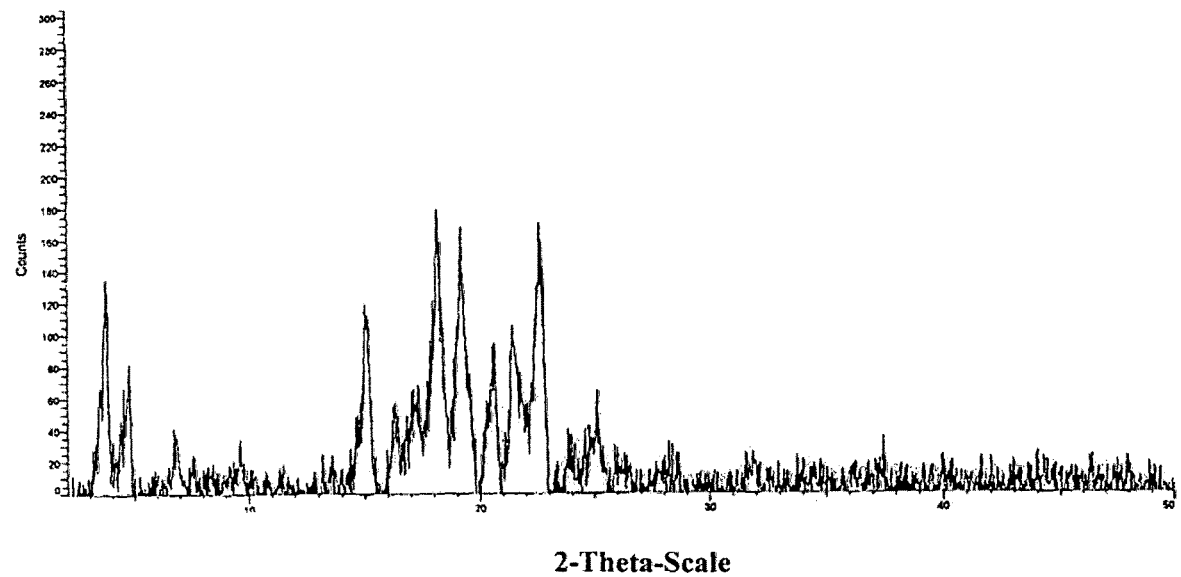
FIG. 1: Illustrates a characteristic PXRD pattern of crystalline form-M of Empagliflozin compound of formula-1.

The present invention relates to novel process for the preparation of D-glucitol, 1,5-anhydro-1-C-[4-chloro-3-[[4-[[(3S)-tetrahydro-3-furanyl]oxy]phenyl]methyl] phenyl]-, (1S) compound of formula-1.

The term "suitable solvent" used in the present invention refers to "hydrocarbon solvents" such as n-hexane, n-heptane, cyclohexane, ether, benzene, toluene, pentane, cycloheptane, methylcyclohexane, ethyl benzene, m-, o-, or p-xylene, octane, indane, nonane, or naphthalene and the like; "ether solvents" such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethylsulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, 2-methoxyethanol, 1, 2-ethoxyethanol, diethylene glycol, 1, 2, or 3-pentanol, neo-pentyl alcohol, t-pentyl alcohol, diethylene glycol monoethyl ether, cyclohexanol, benzyl alcohol, phenol, or glycerol and the like; "polar solvents" such as water or mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia; and organic bases such as triethyl amine, methyl amine, ethyl amine, 1,8-diazabicyclo[5.4.0]undec-7-ene (DBU), 1,5-diazabicyclo(4.3.0)non-5-ene (DBN), lithium dioisoporpylamide (LDA), n-butyl lithium, tribenzylamine, isopropyl amine, diisopropylamine, diisopropylethylamine, N-methylmorpholine, N-ethylmorpholine, piperidine, dimethylaminopyridine, morpholine, pyridine, 2,6-lutidine, 2,4,6-collidine, imidazole, 1-methylimidazole, 1,2,4-triazole, 1,4-diazabicyclo[2.2.2]octane (DABCO) or mixtures thereof.

The suitable hydrochloric acid source is selected from HCl gas, aqueous HCl, dry HCl, ethyl acetate-HCl, IPA-HCl, ethanol-HCl, methanol-HCl and 1,3-dioxane-HCl.

As used herein the term "suitable acid" is selected from formic acid, acetic acid, propionic acid, butanoic acid, pentanoic acid, hexanoic acid, trifluoroacetic acid, methane sulfonic acid, hydrochloric acid and the like.

The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety.

In some embodiments, "hydroxy protecting group (Pg)" is benzyloxycarbonyl (Cbz), 2,2,2-trichloroethoxy carbonyl (Troc), 2-(trimethylsilyl)ethoxycarbonyl (Teoc), 2-(4-trifluoromethylphenylsulfonyl) ethoxycarbonyl (Tsc), t-butoxycarbonyl (BOC), 1-adamantyloxycarbonyl (Adoc), 2-adamantylcarbonyl(2-Adoc), 2,4-dimethylpent-3-yloxycarbonyl (Doc), cyclohexyloxy carbonyl(Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'- dimethylhydrazinyl, methoxymethyl, t-butoxymethyl (Bum), benzyloxymethyl (BOM), or 2-tetrahydropyranyl (THP), 1-(ethoxy)ethyl, p-methoxybenzyl, triphenylmethyl, diphenylmethyl, hydroxymethyl, methoxymethyl, and t-butyldimethylsilylmethyl, N-pivaloyloxymethyl (POM), 1,1-diethoxymethyl, tri(C1-4-alkyl)silyl, p-methoxybenzyl carbonyl (Moz or MeOZ) group, 9-fluorenylmethyloxycarbonyl (FMOC) group, acetyl (Ac) group, benzoyl (Bz) group, Benzyl (Bn) group, p-methoxybenzyl (PMB), 3,4-dimethoxybenzyl.

According to some embodiments, the hydroxy protecting group (Pg) is selected from —C(O)OC$_1$-C$_6$ alkyl, such as, for example, carboethoxy, carbomethoxy and t-butoxycarbonyl; optionally substituted —C(O)OC$_1$-C$_6$ aryl, such as, for example, benzyloxy-carbonyl and p-methoxybenzyloxy-carbonyl; optionally substituted —C$_1$-C$_{12}$ aryl(C$_1$-C$_3$)alkyl such as, for example, benzyl, phenethyl, p-methoxybenzyl, 2,3-dimethoxybenzyl, 2,4-dimethoxybenzyl and 9-fluorenylmethyl; optionally substituted C$_7$-C$_{11}$ aryl carbonyl, such as, for example, benzoyl; C$_1$-C$_6$ alkanoyl, such as, for example, acetyl (also represented as —C(O)CH$_3$ or Ac), propionyl; C$_1$-C$_6$ alkylsulfonyl, such as, for example, methanesulfonyl (mesyl).

The first aspect of the present invention provides a process for the preparation of D-glucitol, 1,5-anhydro-1-C-[4-chloro-3-[[4-[[(3S)-tetrahydro-3-furanyl]oxy]phenyl]methyl]phenyl]-, (1S) compound of formula-1 comprising:

a) Reacting the compound of general formula-7 with suitable thiol reagent in Lewis acid to provide compound of general formula-8;

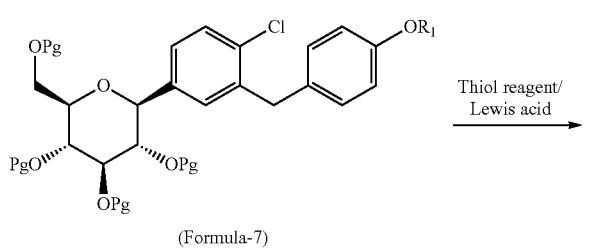

(Formula-7)

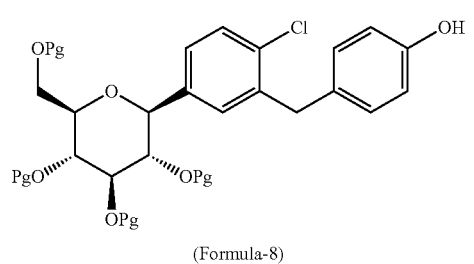

(Formula-8)

b) reacting the compound of general formula-8 with the compound of general formula-11 in presence of a suitable base in a suitable solvent to provide compound of formula-9;

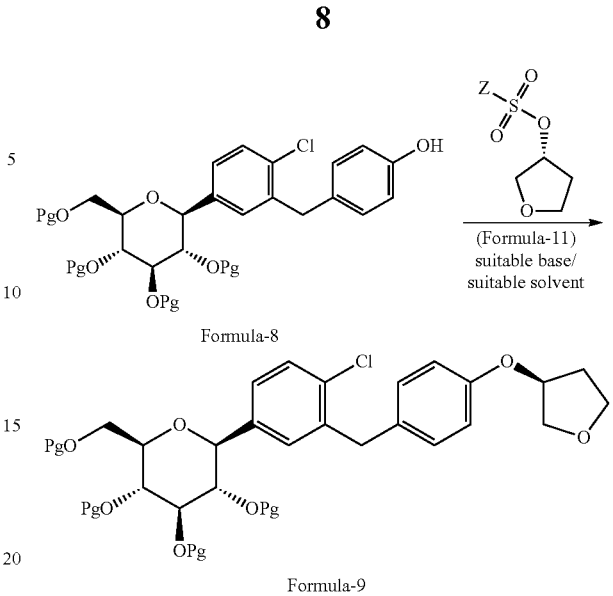

c) deprotecting the product obtained in step-b) to provide the D-glucitol, 1,5-anhydro-1-C-[4-chloro-3-[[4-[[(3S)-tetrahydro-3-furanyl]oxy]phenyl]methyl]phenyl]-, (1S) compound of formula-1.

Formula-9

Empagliflozin of Formula-1 wherein,

R$_1$ is selected from C$_1$-C$_5$ straight or branched chain alkyl group, preferably, —CH$_3$ and Pg is selected from —C(O) OC$_1$-C$_6$ alkyl; optionally substituted —C(O)OC$_1$-C$_6$ aryl; optionally substituted —C$_1$-C$_{12}$ aryl(C$_1$-C$_3$)alkyl; optionally substituted C$_7$-C$_{11}$ aryl carbonyl; C$_1$-C$_6$ alkanoyl; C$_1$-C$_6$ alkylsulfonyl. Preferably, —C(O)CH$_3$.

Z is alkyl group (C$_{1-4}$ carbon atoms) or aryl group (phenyl or naphthyl) substituted with one or more electron withdrawing groups such as —NO$_2$, —NH$_3^+$, —N(R$_1$)$_3$, —CN, —CHO, —COOH, trifluoroalkyl, halogen. Preferably, phenyl group substituted with —NO$_2$ in the ortho or para positions. Most preferably, (R)-tetrahydrofuran-3-yl 4-nitrobenzenesulfonate and (R)-tetrahydrofuran-3-yl 2-nitrobenzenesulfonate.

In step-a), the suitable thiol reagent is selected from thiol or dithiol alcohol such as decanethiol, dodecane thiol, cyclohexane thiol, cyclopentane thiol, cyclo butane thiol, thiophenol, methanethiol, ethanethiol, 1-propanethiol, 2-propanethiol, n-butanethiol, tert-butanthiol, furan-2- ylmethanethiol, ethandithiol, 1,2-propanediol, 1,3-propanediol, 1,3-butanediol, 1,4-butanediol; suitable Lewis acid is selected from aluminium trihalides such as $AlCl_3$, $AlBr_3$ and the like, boron trihalides such as $BCl_3$ and the like, $TiCl_4$, $FeCl_3$, $ZnCl_2$ and the like.

In step-b), the suitable base is selected from inorganic base "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like.

In step-c), the deprotection is carried out using suitable base or suitable mineral acid in a suitable solvent. Wherein, the suitable base is same as the base used in step-b). The suitable mineral acid is selected from hydrochloric acid, hydrobromic acid, nitric acid, sulphuric acid, nitric acid, acetic acid or mixture of their aqueous mixtures thereof.

In step-a) to step-c), the suitable solvent is selected from alcohol solvents such as methanol, ethanol, n-propanol, i-propanol, butanol; chloro solvents such as methylene chloride, chloroform, carbon tetrachloride; ketone solvents such as acetone, butanone; nitrile solvents such as acetonitrile, propionitrile, butyronitrile; ester solvents such as ethyl acetate, methyl acetate, butyl acetate; hydrocarbon solvents such as heptane, hexane, benzene, toluene, xylene; ether solvents such as diethyl ether, methyl tert-butyl ether, tetrahydrofuran, 1,4-diethyl ether or mixture thereof.

In order to overcome the problems associated with prior known processes, the inventors of the present invention carried out the deprotection by using thiols or dithiols in presence of Lewis acids. They have observed that, the desired hydroxy compound was obtained with high yield and purity.

The advantages of the process include simple, eco-friendliness and suitable for commercial use.

In another aspect of the present invention provides a process for the preparation of D-glucitol, 1,5-anhydro-1-C-[4-chloro-3-[[4-[[(3S)-tetrahydro-3-furanyl]oxy]phenyl]methyl]phenyl]-, (1S) compound of formula-1 comprising:

a) Reacting the compound of formula-7a with dodecanethiol in presence of $AlCl_3$ to get the compound of general formula-8a;

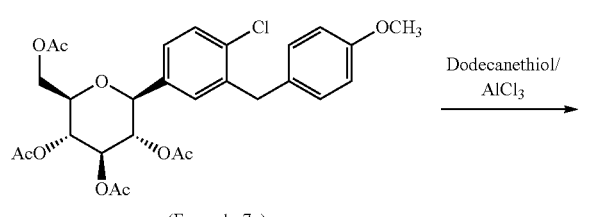

b) reacting the compound of general formula-8a with (R)-tetrahydrofuran-3-yl 4-nitrobenzenesulfonate in presence of $K_2CO_3$ in dimethylformamide to provide compound of formula-9a;

c) deprotecting the product obtained in step-b) to provide the D-glucitol, 1,5-anhydro-1-C-[4-chloro-3-[[4-[[(3S)-tetrahydro-3-furanyl]oxy]phenyl]methyl]phenyl]-, (1S) compound of formula-1.

Another aspect of the present invention provides an improved process for the preparation of D-glucitol, 1,5-anhydro-1-C-[4-chloro-3-[[4-[[(3S)-tetrahydro-3-furanyl]oxy]phenyl] methyl] phenyl]-, (1S) compound of formula-1 comprising:

a) Reducing the compound of general formula-2 using suitable reducing agent in presence of titanium tetrachloride ($TiCl_4$) in a suitable solvent to provide the compound of general formula-3;

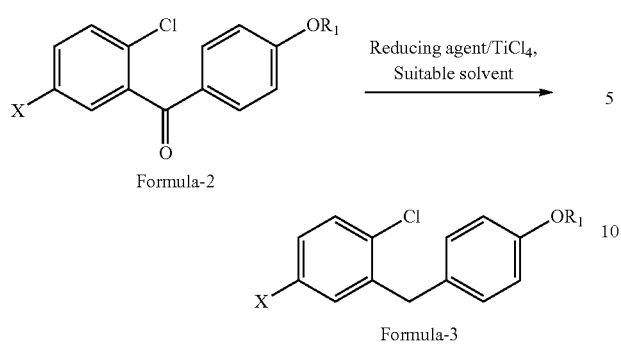

Formula-2

Reducing agent/TiCl₄, Suitable solvent

Formula-3 wherein, $R_1$ is same as defined above; X is bromo or iodo.

b) reacting the compound of general formula-3 with the compound of formula-4 in presence of organolithium followed by treating with an acid in a suitable solvent to provide the compound of general formula-5;

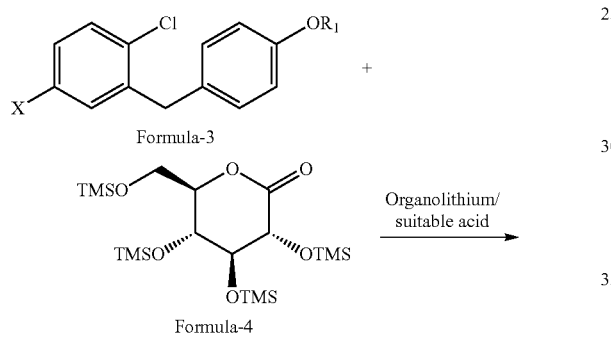

Formula-3

Formula-4

Organolithium/ suitable acid

Formula-5 wherein, R is hydrogen or same as $R_1$ as defined above.

c) optionally isolating the product obtained in step-b;

d) reducing the product obtained in step-b) or step-c) with a suitable reducing agent in a suitable solvent to provide the compound of general formula-6;

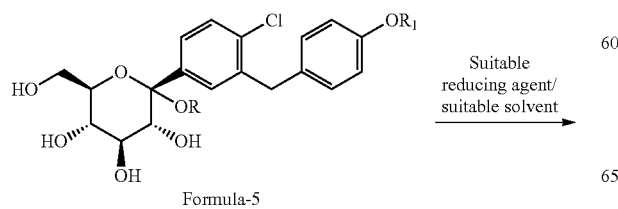

Formula-5

Suitable reducing agent/ suitable solvent

-continued

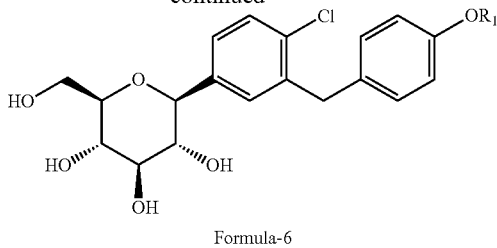

Formula-6 e) optionally, isolating the product obtained in step-d);

f) reacting the product obtained in step-d) or step-e) with a suitable protecting agent in presence of a suitable base in a suitable solvent to provide the compound of general formula-7;

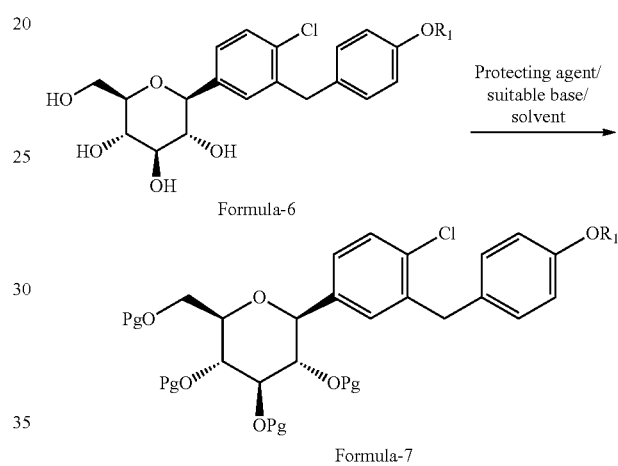

Formula-6

Protecting agent/ suitable base/ solvent

Formula-7 wherein, Pg is a protecting group.

g) reacting the compound of general formula-7 with suitable thiol reagent in presence of a suitable catalyst to provide the compound of general formula-8;

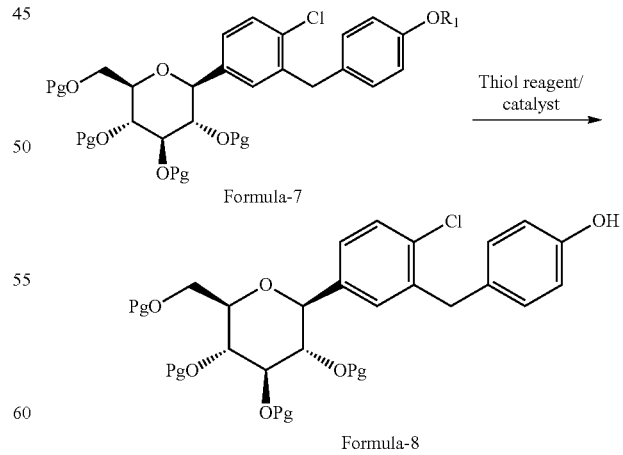

Formula-7

Thiol reagent/ catalyst

Formula-8 h) reacting the compound of general formula-8 with the compound of formula-11 in presence of a suitable base in a suitable solvent to provide the compound of general formula-9;

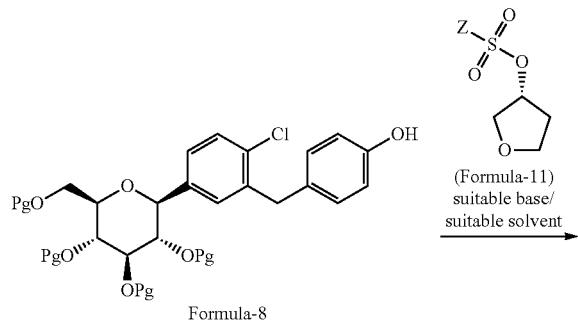

Formula-8 + (Formula-11) suitable base/ suitable solvent →

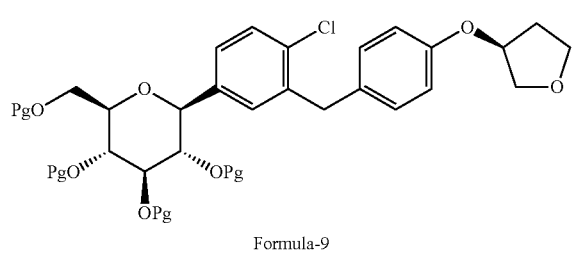

Formula-9 i) deprotecting the compound of general formula-9 in presence of suitable base in suitable solvent to provide the compound of formula-1.

Formula-9 — Deprotection →

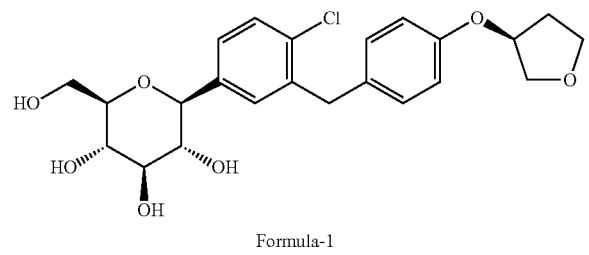

Formula-1 wherein, in step-a), the suitable reducing agent is selected from trialkylsilyl hydrides, hydrogen gas in presence of Pd, Pt, Raney Ni, Fe and the like; the suitable metal catalyst is $TiCl_4$; the suitable solvent is selected from halohydrocarbon solvents, ether solvents, ester solvents, polar-aprotic solvents or the mixture of solvents thereof;

in step-b), the organolithium compound is selected from n-butyl lithium, t-butyl lithium and the like; the suitable acid is selected from mineral acids such as aqueous hydrochloric acid, hydrobromic acid and the like or organic acids such as alkyl sulfonic acids, aryl sulfonic acids. This step may optionally carried out in presence of suitable solvent which is selected from water and alcohol solvents having $C_1$-$C_5$ carbon atoms.

In step-d), the suitable reducing agent is selected from trialkyl silylhydride such as trimethylsilyl hydride, triethylsilylhydride, tributylsilylhydride and the like; the suitable solvent is selected from acetonitrile, dimethylformamide, dimethylsulfoxide, dimethylacetamide, dichloromethane, chlorobenzene, chloroform, toluene, xylene, benzene, ethyl acetate, methyl acetate, propyl acetate, diethylether, tert-butylmethyl ether, tetrahydrofuran or the mixture of solvents thereof.

In step-f), the suitable protecting agent is $R_1$—C(O)—Cl, wherein $R_1$ is same as defined above; the suitable base is selected from dimethylaminopyridine, triethylamine, diisopropylethylamine, diethylamine, ammonia and the like; the suitable solvent is as defined above.

In step-g), the suitable thiol agent is selected from decanethiol, dodecane thiol, cyclohexane thiol, cyclopentane thiol, cyclo butane thiol, thiophenol, methanethiol, ethanethiol, 1-propanethiol, 2-propanethiol, n-butanethiol, tert-butanthiol, furan-2-ylmethanethiol, ethandithiol, 1,2-propanedithiol, 1,3-propanedithiol, 1,3-butanedithiol, 1,4-butanedithiol; suitable Lewis acid is selected from aluminium trihalides such as $AlCl_3$, $AlBr_3$ and the like, boron trihalides such as $BF_3$, $BCl_3$, and the like; $TiCl_4$, $FeCl_3$, $ZnCl_2$ and the like.

In step-f) and h), the suitable base is an inorganic base which is selected from sodium hydroxide, sodium carbonate, sodium bicarbonate, potassium hydroxide, potassium carbonate, potassium bicarbonate, sodium hydride and the like; the suitable solvent is selected from alcohol solvents, chloro solvents, ketone solvents, polar aprotic solvents, nitrile solvents, ester solvents, hydrocarbon solvents, ether solvents and polar solvents like water or mixture thereof.

In step-i), the deprotection is carried out in presence of suitable base or suitable mineral acid. The suitable inorganic base is selected from sodium hydroxide, sodium carbonate, sodium bicarbonate, potassium hydroxide, potassium carbonate, potassium bicarbonate, sodium hydride and the like. The suitable mineral acid is selected from hydrochloric acid, hydrobromic acid, sulfuric acid, acetic acid, nitric acid or their aqueous solvents. The suitable solvent is selected from alcohol solvents, chloro solvents, ketone solvents, polar aprotic solvents, nitrile solvents, ester solvents, hydrocarbon solvents, ether solvents and polar solvents like water or mixture thereof.

In another aspect of the present invention provides an improved process for the preparation of D-glucitol, 1,5-anhydro-1-C-[4-chloro-3-[[4-[[(3S)-tetrahydro-3-furanyl]oxy]phenyl] methyl] phenyl]-, (1S) compound of formula-1 comprising:

a) Reducing the compound of formula-2a with triethylsilylhydride in presence of titanium tetrachloride (TiCl₄) in methylene chloride to provide the compound of formula-3a;

b) reacting the compound of formula-3a with the compound of formula-4 in presence of n-butyl lithium followed by treating with aqueous HCl and water to provide the compound of formula-5a;

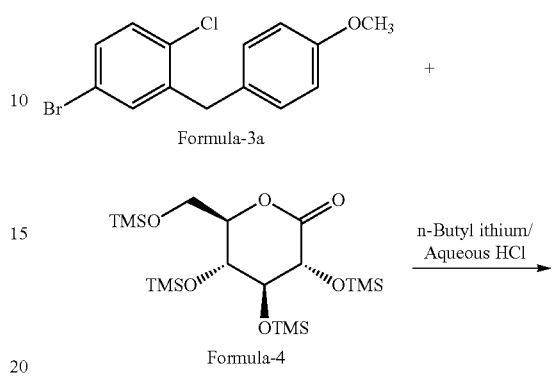

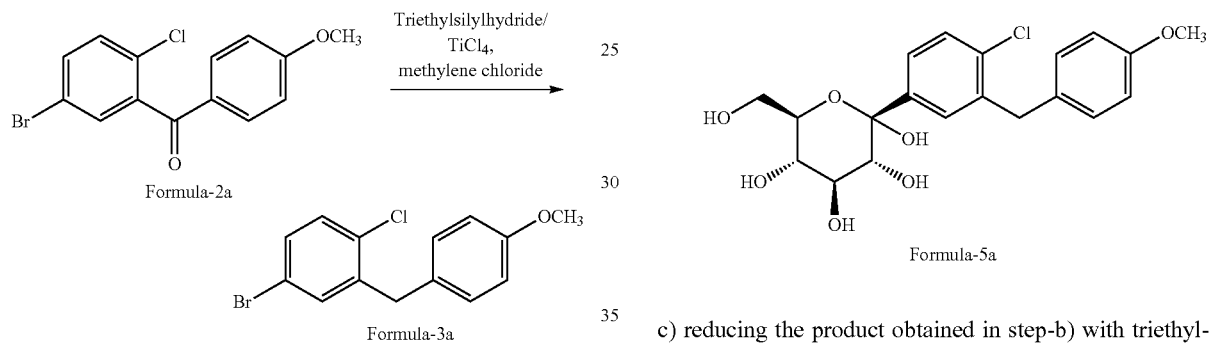

c) reducing the product obtained in step-b) with triethylsilylhydride in presence of BF₃.etherate to provide the compound of formula-6a;

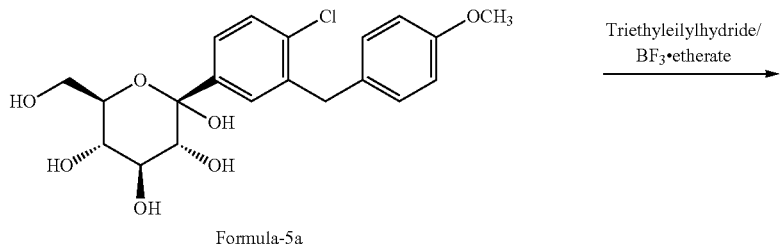

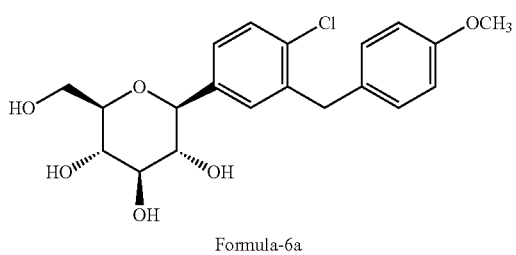

d) reacting the product obtained in step-c) with aceticanhydride, dimethylaminopyridine (DMAP) in methylene chloride to provide the compound of formula-7a;

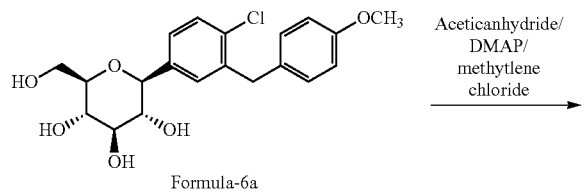

e) reacting the compound of formula-7a with dodecanethiol in $AlCl_3$ to provide the compound of formula-8a;

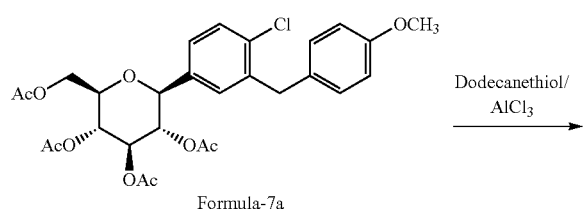

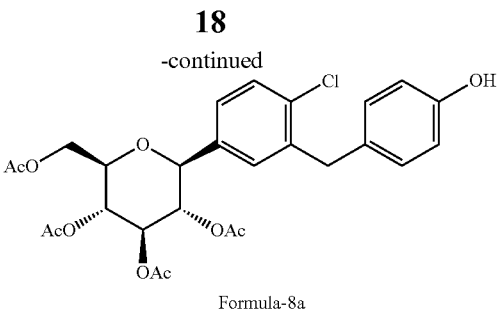

f) reacting the compound of formula-8a with (R)-tetrahydrofuran-3-yl 4-nitrobenzenesulfonate in presence of $K_2CO_3$ in dimethylformamide to provide the compound of formula-9a;

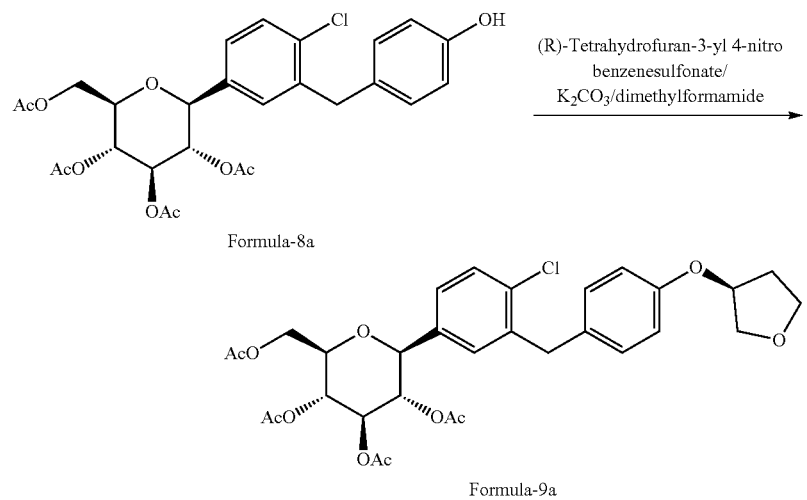

g) deprotecting the compound of formula-9a to provide the compound of formula-1.

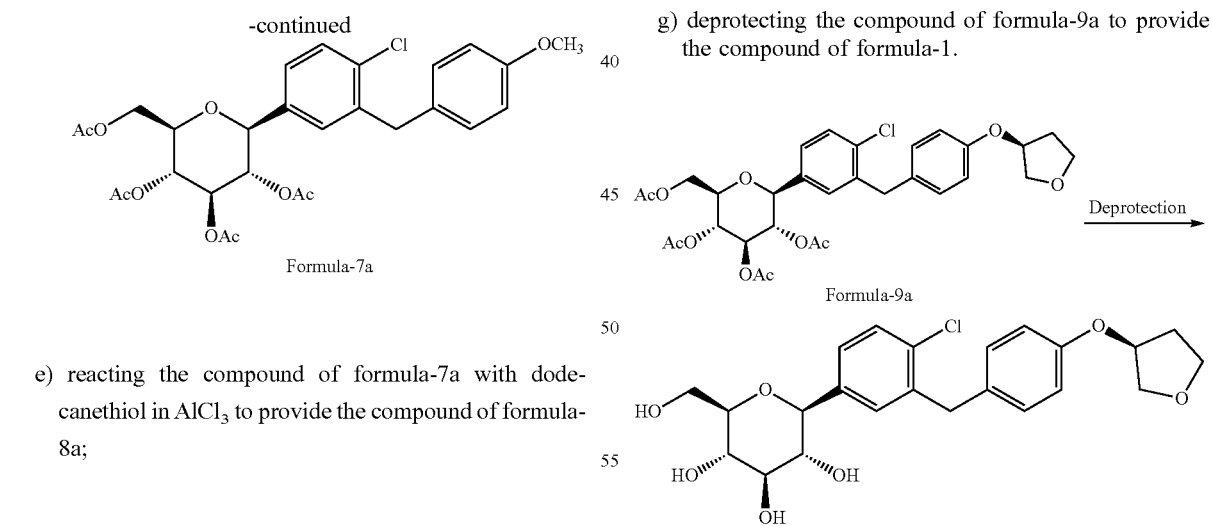

The second aspect of the present invention provides a process for the preparation of the compound of general formula-8, comprising: reacting the compound of general formula-7 with thiol reagent in presence of Lewis acid catalyst in a suitable solvent to provide the compound of general formula-8.

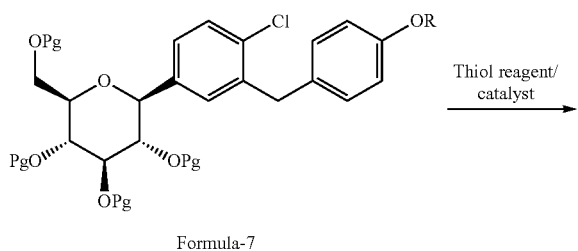

Formula-7

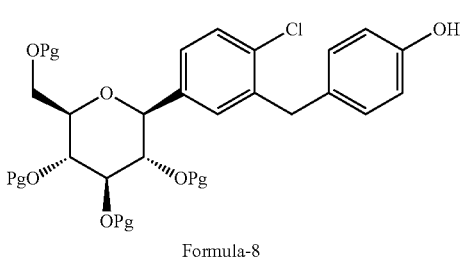

Formula-8 wherein, Pg is same as defined above.

Another aspect of the present invention provides an alternative process for the preparation of the compound of general formula-8 comprising: treating the compound of general formula 2' with suitable deacylating agent in a suitable organic solvent to produce the compound of general of formula-8.

The process is schematically shown as below:

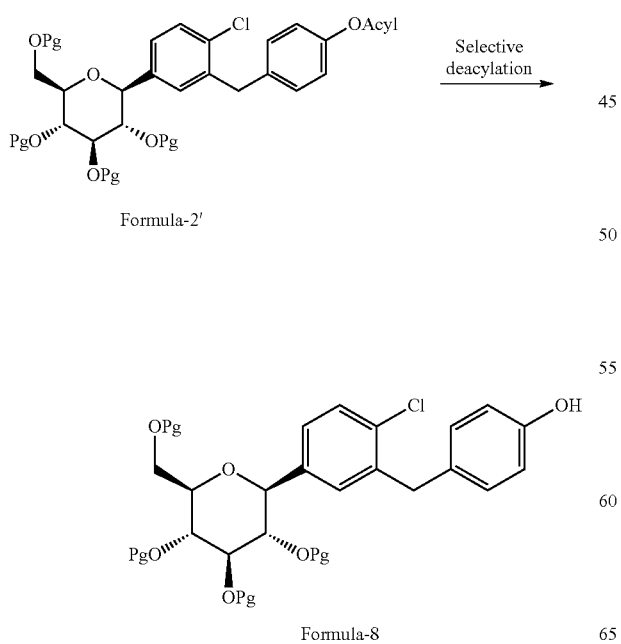

wherein, the acyl group is selected from —(CO)$R_2$, wherein $R_2$ is $C_1$-$C_5$ straight chain or branched substituted or unsubstituted alkyl groups, phenyl, benzyl and the like; deacylating agent is selected from ammonium acetate, sodium sulfite preferably ammonium acetate.

According to the prior known processes, the separation of isomers from the racemic penta hydroxy compound was carried out using preparative HPLC method and further the obtained compounds were purified using column chromatography. Since the said process is quite tedious, time consuming and not suitable on commercial scale up.

In another aspect of present invention provides an improved process for the preparation of pure D-glucitol, 1,5-anhydro-1-C-[4-chloro-3-[[4-[[(3S)-tetrahydro-3-furanyl]oxy]phenyl] methyl] phenyl]-, (1S) compound of formula-1 comprising:

a) reacting (2S,3R,4R,5S,6R)-2-(4-chloro-3-(4-hydroxy-benzyl)phenyl)-6-(hydroxy-methyl)tetrahydro-2H-pyran-3,4,5-triol formula-13 with silylating agent of formula Si($R_1$)($R_3$)($R_4$)Cl in presence of suitable base in a suitable solvent to provide the compound of general formula-14;

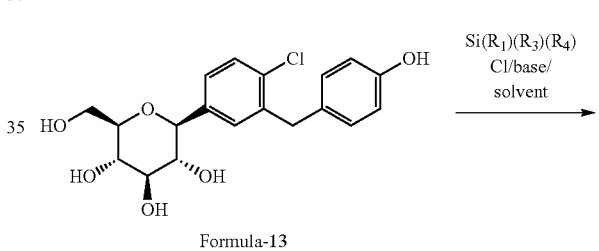

Formula-13

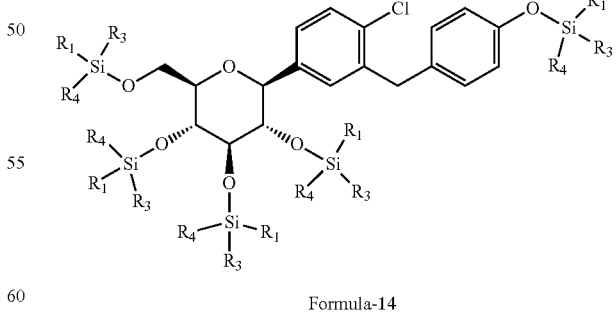

Formula-14 b) reacting the compound of general formula-14 with the compound of general formula-11 in presence of a suitable base in a suitable solvent to provide the compound of formula-1.

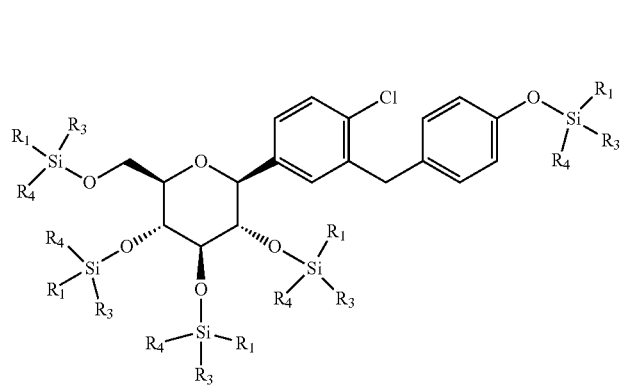

Formula-14

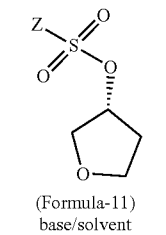

(Formula-11)
base/solvent
→

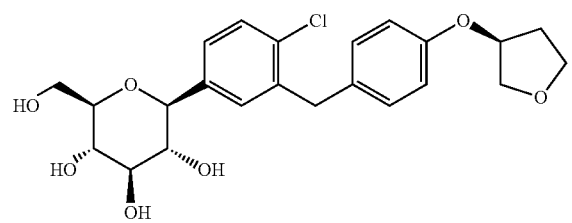

Formula-1 wherein, $R_1$, $R_3$ and $R_4$ are independently of one another denote $C_{1-4}$-alkyl, aryl or aryl-$C_{1-3}$-alkyl, while the alkyl groups may be mono- or polysubstituted by halogen.

The suitable base is selected from N-methyl morpholine (NMP), diisopropylethylamine, pyridine, dimethylaminopyridine, sodium hydroxide, sodium carbonate, sodium bicarbonate, potassium hydroxide, potassium carbonate, potassium bicarbonate, sodium hydride and the like; the suitable solvent is selected from tetrahydrofuran, acetonitrile, ethyl acetate, methyl acetate, methyl tert-butyl ether, $C_{1-5}$ alcohol solvents and the like.

Further, the present invention provides an improved process for the preparation of pure D-glucitol, 1,5-anhydro-1-C-[4-chloro-3-[[4-[[(3S)-tetrahydro-3-furanyl]oxy]phenyl]methyl] phenyl]-, (1S) compound of formula-1 comprising:

a) Reacting (2S,3R,4R,5S,6R)-2-(4-chloro-3-(4-hydroxybenzyl)phenyl)-6-(hydroxy-methyl)tetrahydro-2H-pyran-3,4,5-triol of formula-13 with trimethylchlorosilane in presence of N-methyl morpholine in tetrahydrofuran to produce (((2S,3S,4R,5R,6R)-2-(4-chloro-3-(4-((trimethylsilyl)oxy)benzyl)phenyl)-6-(((trimethylsilyl)oxy)methyl) tetrahydro-2H-pyran-3,4,5-triyl)tris(oxy))tris(trimethylsilane) of formula-14a;

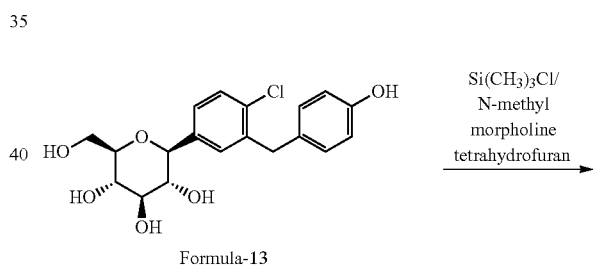

Formula-13

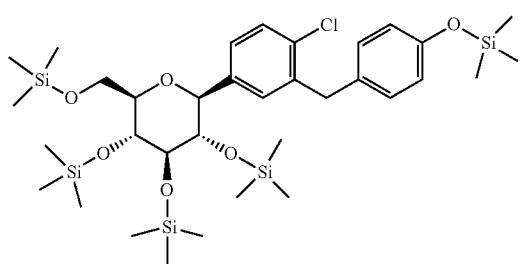

Formula-14a b) reacting the compound of formula-14a with (R)-tetrahydrofuran-3-yl 4-nitrobenzenesulfonate in presence of $K_2CO_3$ in acetonitrile to produce D-glucitol, 1,5-anhydro-1-C-[4-chloro-3-[[4-[[(3S)-tetrahydro-3-furanyl]oxy]phenyl]methyl]phenyl]-, (1S) of formula-1

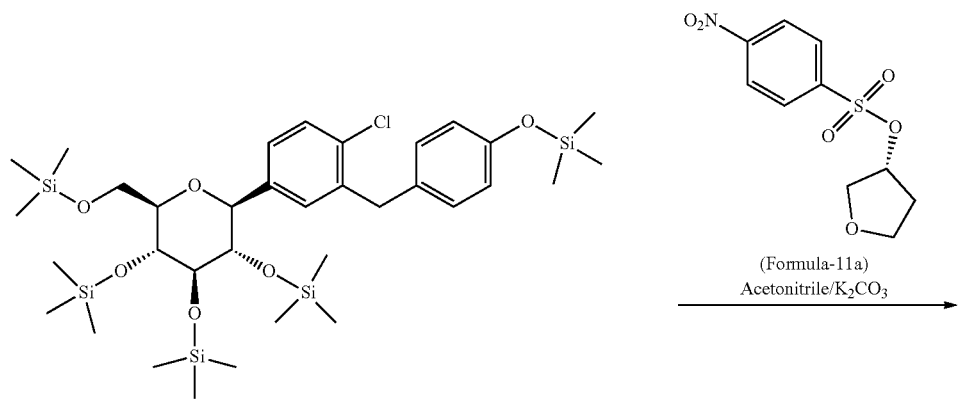

Formula-14a

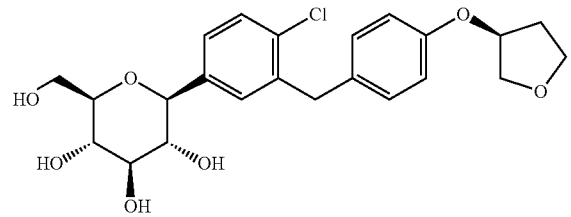

(Formula-11a)
Acetonitrile/K₂CO₃

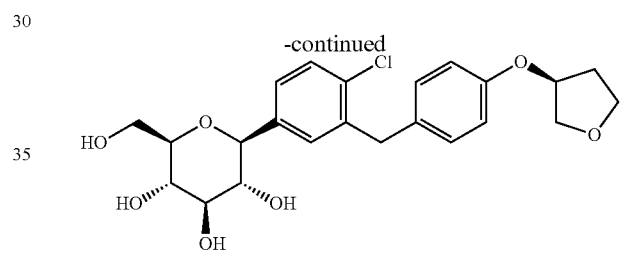

Formula-1

The HPLC purity of D-glucitol, 1,5-anhydro-1-C-[4-chloro-3-[[4-[[(3S)-tetrahydro-3-furanyl]oxy]phenyl]methyl]phenyl]-, (1S) formula-1 obtained by the above process is 99.39%.

In another aspect of present invention provides an improved process for the preparation of pure D-glucitol, 1,5-anhydro-1-C-[4-chloro-3-[[4-[[(3S)-tetrahydro-3-furanyl]oxy]phenyl] methyl] phenyl]-, (1S) compound of formula-1 comprising: reacting the compound of general formula-15 with the compound of general formula-11 in presence of suitable base in a suitable solvent.

The process is schematically shown as below:

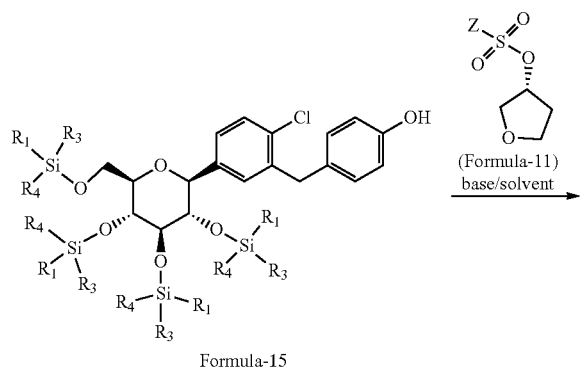

Formula-15

(Formula-11)
base/solvent

-continued

Formula-1 wherein, the suitable base is selected from N-methyl morpholine (NMP), diisopropylethylamine, pyridine, dimethylaminopyridine, sodium hydroxide, sodium carbonate, sodium bicarbonate, potassium hydroxide, potassium carbonate, potassium bicarbonate, sodium hydride and the like; the suitable solvent is selected from tetrahydrofuran, acetonitrile, ethyl acetate, methyl acetate, methyl tert-butyl ether, $C_{1-5}$ alcohol solvents and the like.

Further, yet another aspect of present invention provides an improved process for the preparation of D-glucitol; 1,5-anhydro-1-C-[4-chloro-3-[[4-[[(3S)-tetrahydro-3-furanyl]oxy]phenyl] methyl] phenyl]-, (1S) compound of formula-1 comprising: reacting 4-(2-chloro-5-((2S,3S,4R,5R,6R)-3,4,5-tris((trimethylsilyl)oxy)-6-(((trimethylsilyl)oxy) methyl) tetrahydro-2H-pyran-2-yl)benzyl)phenol of formula-15a with (R)-tetrahydrofuran-3-yl 4-nitrobenzenesulfonate in presence of K₂CO₃ in acetonitrile to produce D-glucitol, 1,5-anhydro-1-C-[4-chloro-3-[[4-[[(3S)-tetrahydro-3-furanyl]oxy]phenyl]methyl]phenyl]-, (1S) of formula-1

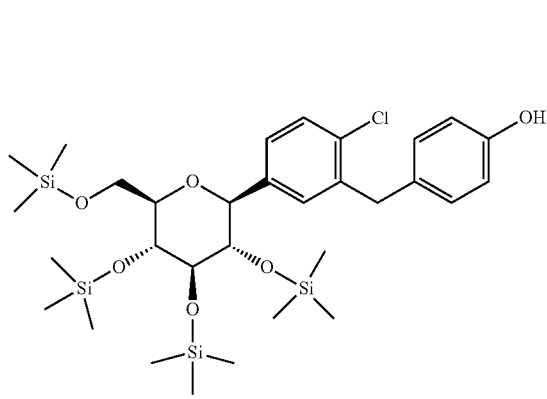

Formula-15a

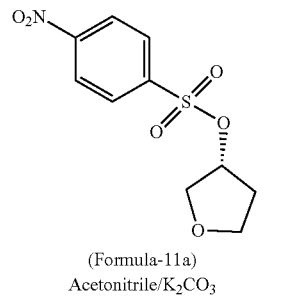

(Formula-11a)
Acetonitrile/K₂CO₃
→

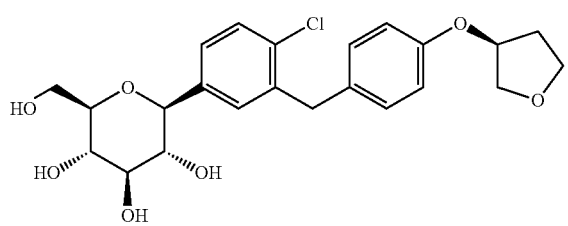

Formula-1

The third aspect of the present invention provides an improved process for the preparation of the compound of formula-10, comprising: reacting the compound of general formula-3 with thiol reagent in presence of Lewis acid in a suitable solvent (or) reacting with aqueous hydrobromic acid and $C_1$-$C_3$ carboxylic acid in a suitable organic solvent
The process is schematically shown as below:

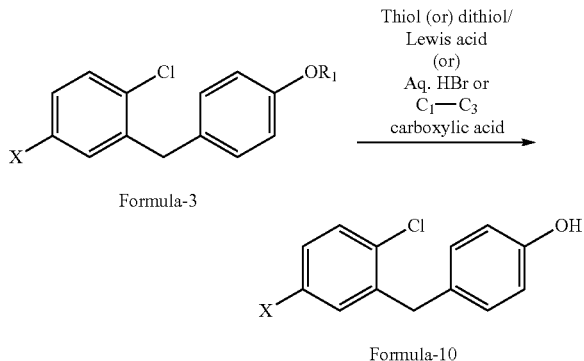

wherein, $R_1$ and X are defined as above.

The alkoxy compound of general formula-3 is reacted with dodecanethiol in presence of aluminium chloride in dichloromethane at room temperature to produce the required hydroxy compound of formula-10.

In order to overcome the problems associated with prior known processes, the inventors of the present invention carried out the deprotection by using thiols or dithiols in presence of Lewis acids. They have observed that, the desired hydroxy compound was obtained with high yield and purity.

The advantages of the process include simple, eco-friendliness and suitable for commercial use.

The fourth aspect of the present invention provides the compound of formula-11.

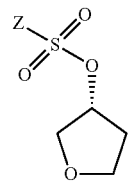

Formula-11 wherein, Z is alkyl group ($C_{1-4}$ carbon atoms) or aryl group (phenyl or naphthyl) substituted with one or more electron withdrawing groups such as —NO₂, —NH₃⁺, —N(R₁)₃, —CN, —CHO, —COOH, trifluoroalkyl, halogen. Preferably, phenyl group substituted with —NO₂ in the ortho or para positions. Most preferably, solid compounds of (R)-tetrahydrofuran-3-yl 4-nitrobenzenesulfonate and (R)-tetrahydrofuran-3-yl 2-nitrobenzenesulfonate.

In another aspect of the present invention provides the solid compound of formula-11 can be used in the synthesis of D-glucitol, 1,5-anhydro-1-C-[4-chloro-3-[[4-[[(3S)-tetrahydro-3-furanyl]oxy]phenyl] methyl] phenyl]-, (1S).

The fifth aspect of the present invention provides a process for the preparation of compound of formula-11, comprising: reacting the (R)-tetrahydrofuran-3-ol with compound of general formula-12 in presence of suitable base and suitable solvent to provide the compound of formula-11.

The process is schematically shown as below:

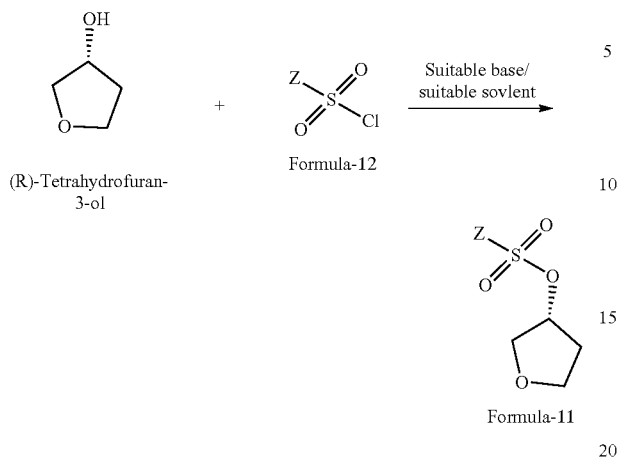

wherein, Z is same as defined above; the suitable base is organic base or inorganic base which are selected from dimethylaminopyridine (DMAP), triethylamine, trimethylamine, tripropylamine, diisopropylethylamine (DIPEA), pyridine, N-methyl morpholine (NMM) or mixtures thereof; the inorganic base is selected from sodium hydroxide, sodium carbonate, sodium bicarbonate, potassium hydroxide, potassium carbonate, potassium bicarbonate, sodium hydride and the like; the suitable solvent is selected from methylene chloride, methanol, ethanol, isopropanol, n-butanol, isobutanol, ethyl acetate, methyl acetate, propyl acetate, acetonitrile, dimethyl formamide, dimethylacetamide, diethyl ether, methyl tert-butyl ether, tetrahydrofuran and the like.

In another aspect of the present invention provides a process for the preparation of (R)-tetrahydrofuran-3-yl 4-nitrobenzenesulfonate of formula-11a, comprising: reacting (R)-tetrahydrofuran-3-ol with 4-nitrobenzene-1-sulfonyl chloride in presence dimethylaminopyridine, triethylamine and methylene chloride.

The process is schematically shown as below:

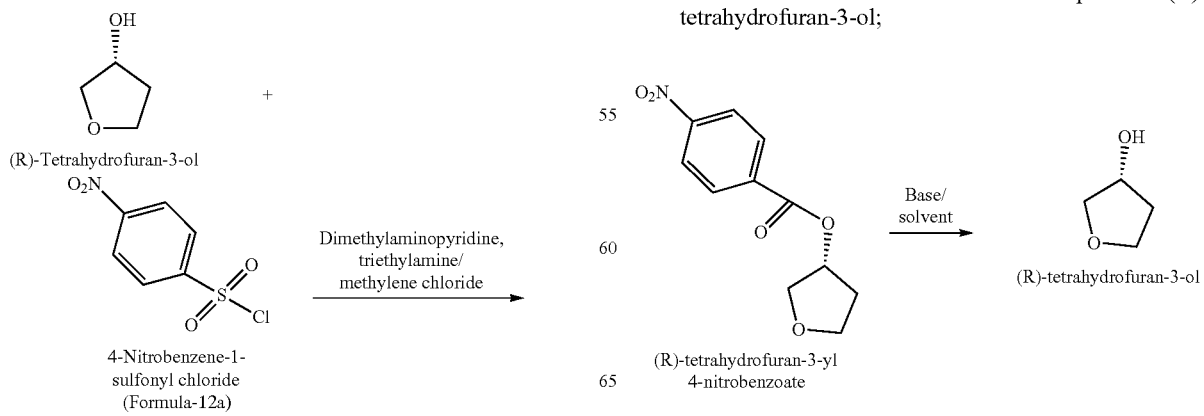

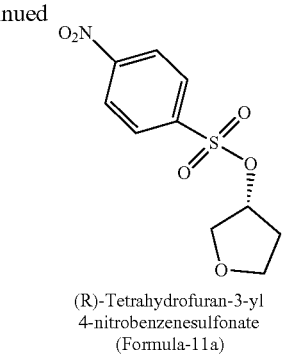

In another aspect of the present invention provides a process for the preparation of the compound of formula-11, comprising:
a) Reacting (S)-tetrahydrofuran-3-ol with p-nitrobenzoic acid in presence of triphenylphosphine and diisopropyl azodicarboxylate in a suitable solvent;

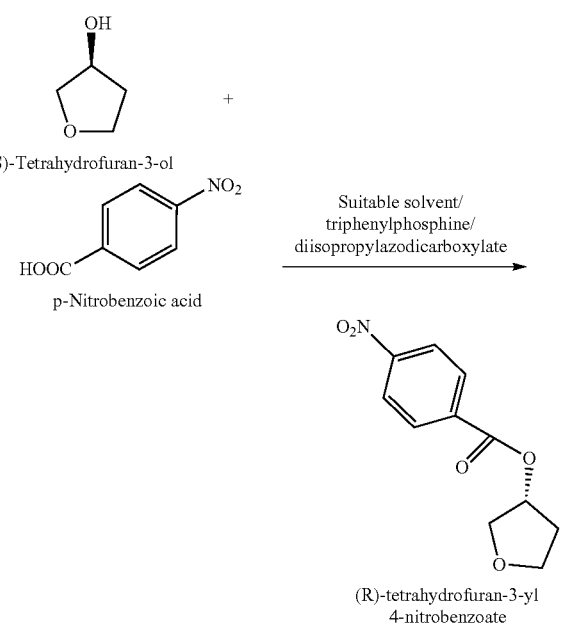

b) treating the (R)-tetrahydrofuran-3-yl 4-nitrobenzoate with a base in a suitable solvent to produce (R)-tetrahydrofuran-3-ol;

c) reacting the (R)-tetrahydrofuran-3-ol with sulfonyl chloride of formula-12 in presence of suitable base and suitable solvent to provide the compound of formula-11.

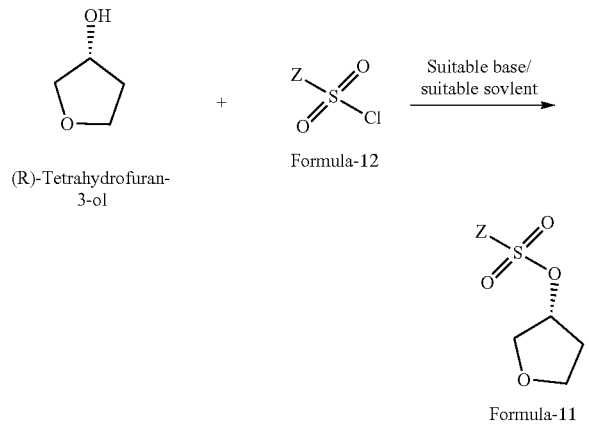

Wherein, Z is same as defined above; suitable sol rent used in step-a) and step-b) is selected from ether solvents such as tetrahydrofuran, diethyl ether, diisopropyl ether, methyl tert-butyl ether and the like; ester solvents such as methyl acetate, ethyl acetate and isopropyl acetate; nitrile solvents such as acetonitrile, propionitrile and the like; halo hydrocarbon solvents such as methylene chloride, chloroform and the like; alcohol solvents such as methanol, ethanol, n-propanol or isopropanol and the like the suitable base is organic base or inorganic base which are selected from dimethylaminopyridine (DMAP), triethylamine, trimethylamine, tripropylamine, triisopropylamine, diisopropylethylamine (DIPEA), pyridine, N-methyl morpholine (NMM) or mixtures thereof; the inorganic base is selected from sodium hydroxide, sodium carbonate, sodium bicarbonate, potassium hydroxide, potassium carbonate, potassium bicarbonate, sodium hydride and the like; the suitable solvent is selected from methylene chloride, methanol, ethanol, isopropanol, n-butanol, isobutanol, ethyl acetate, methyl acetate, propyl acetate, acetonitrile, dimethyl formamide, dimethylacetamide, diethyl ether, methyl tert-butyl ether, tetrahydrofuran and the like.

The sixth aspect of the present invention provides crystalline form-M of Empagliflozin. Crystalline form-M of Empagliflozin is characterized by Powdered X-Ray Diffraction (PXRD) peaks at about 15.0, 18.1, 22.5±0.2° of two-theta. Crystalline form-M of Empagliflozin is further characterized by PXRD additional peaks at 3.6, 4.6, 6.8, 7.5, 16.3, 17.2, 20.5, 21.4, 23.8, 25.0±0.2° of two-theta. Further, crystalline form-M of Empagliflozin is characterized by PXRD pattern as shown in FIG. 1.

The present invention further provides a process for the preparation of crystalline form-M of Empagliflozin, comprising of:
  a) suspending Empagliflozin in a suitable solvent,
  b) heating the reaction mixture of step-a) to a suitable temperature,
  c) adding suitable anti-solvent to the reaction mixture of step-b) at a suitable temperature,
  d) stirring the reaction mixture of step-c) at a suitable temperature,
  e) isolating the crystalline form-M of Empagliflozin.

wherein,
in step-a), the suitable solvent is selected from ester solvents, hydrocarbon solvents, polar aprotic solvents, alcohol solvents having $C_1$-$C_5$ carbon atoms, chloro solvents, or mixtures thereof;
in step-b), the suitable temperature used is ranging from 30° C. to 85° C.;
in step-c), the suitable anti-solvent is selected from hydrocarbons solvents, ether solvents;
in step-c) and step-d), the suitable temperature is ranging from −50° C. to −40° C.;
in step-e), the isolation is carried out by distilling off the solvent from the obtained reaction mixture from step-d) to afford the crystalline form-M of Empagliflozin.

In another aspect of the present invention provides particle size distribution of amorphous form of Empagliflozin of formula-1 having D(90) less than 200 μm, preferably 189.4. D(50) less than 100, preferably less than 70.6 μm. D(10) less than 20, preferably 17.0 μm.

In another aspect of the present invention provides a process for the preparation of amorphous form of Empagliflozin of formula-1, comprising:
  a) adding Empagliflozin to a suitable solvent,
  b) stirring the reaction mixture of step-a) at a suitable temperature,
  c) isolating amorphous form of Empagliflozin wherein,
in step-a) the suitable solvent is selected from alcohol solvents having $C_1$-$C_5$ carbon atoms, ester solvents, ketone solvents having $C_3$-$C_5$ carbon atoms, chloro solvents, or mixtures thereof;
in step-b), the suitable temperature is ranging from 25° C. to the reflux temperature of the solvent used, preferably at 25-30° C.;
in step-c), isolation can be carried out by the distillation under reduced pressure at a suitable temperature ranging from about 30-60° C.

After distillation, the obtained solid compound was dried to provide amorphous Empagliflozin.

Another aspect of the present invention also provides Empagliflozin pharmaceutical composition comprising an amorphous form of Empagliflozin with pharmaceutically acceptable excipients.

The pharmaceutically acceptable excipients are selected from hydroxy propyl cellulose (HPC), cross-povidone and the like.

Figure 4:
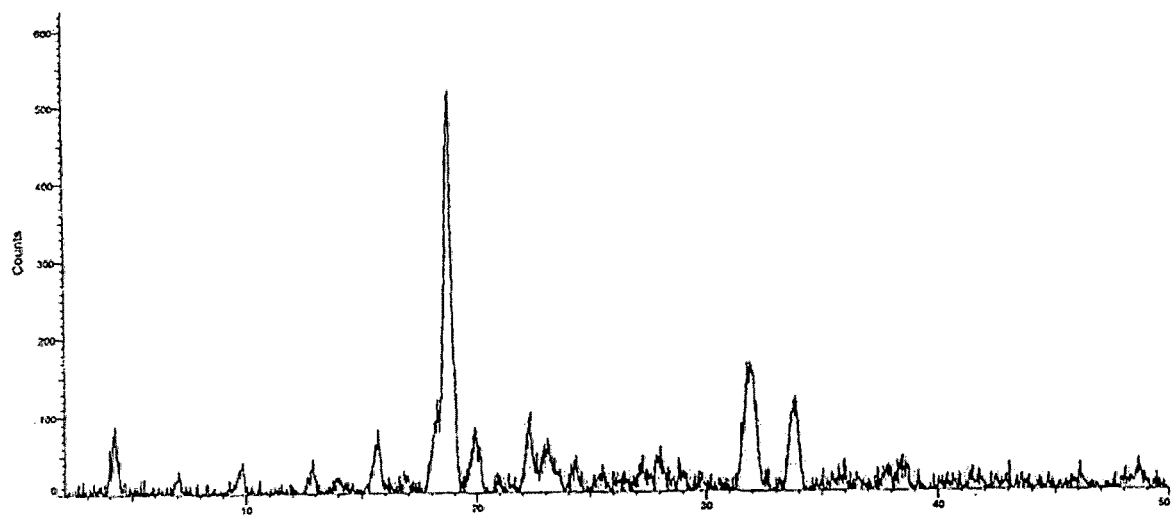
FIG. 4: Illustrates a characteristic PXRD pattern of crystalline Form-I of Empagliflozin-L-proline.

The seventh aspect of the present invention provides crystalline Form-I of Empagliflozin-L-proline. Crystalline Form-I of Empagliflozin-L-proline is characterized by PXRD peaks at about 19.9, 31.9 and 33.8±0.2° of two-theta. Crystalline Form-I of Empagliflozin-L-proline is further characterized by PXRD additional peaks at about 4.2, 15.6, 18.7, 19.9, 22.3, 31.9, 33.8±0.2° of two-theta. Crystalline Form-I of Empagliflozin-L-proline is characterized by PXRD pattern as illustrated in FIG. 4.

Further, another aspect of the present invention also provides a process for the preparation of crystalline Form-I of Empagliflozin-L-proline, comprising:
  a) suspending Empagliflozin and L-proline in one or more organic solvents;
  b) heating to a suitable temperature;
  c) stirring at suitable temperature;
  d) cooling the reaction mixture to 25-30°;
  e) stirring the reaction mixture at 25-30°;
  f) isolating crystalline Form-I of Empagliflozin-L-proline.

Wherein,

In step-a), the suitable organic solvent is selected from isopropanol, dichloromethane, chlorobenzene, tetrahydrofuran or their mixtures thereof.

In step-b) & step-c), the suitable temperature is about 60° C. to 65° C.

In step-e), the stirring is carried out for 5-6 hours at 25-30° temperature.

In step-f), the isolation can be carried out by removing the solvent either by filtration or distillation.

Figure 5:
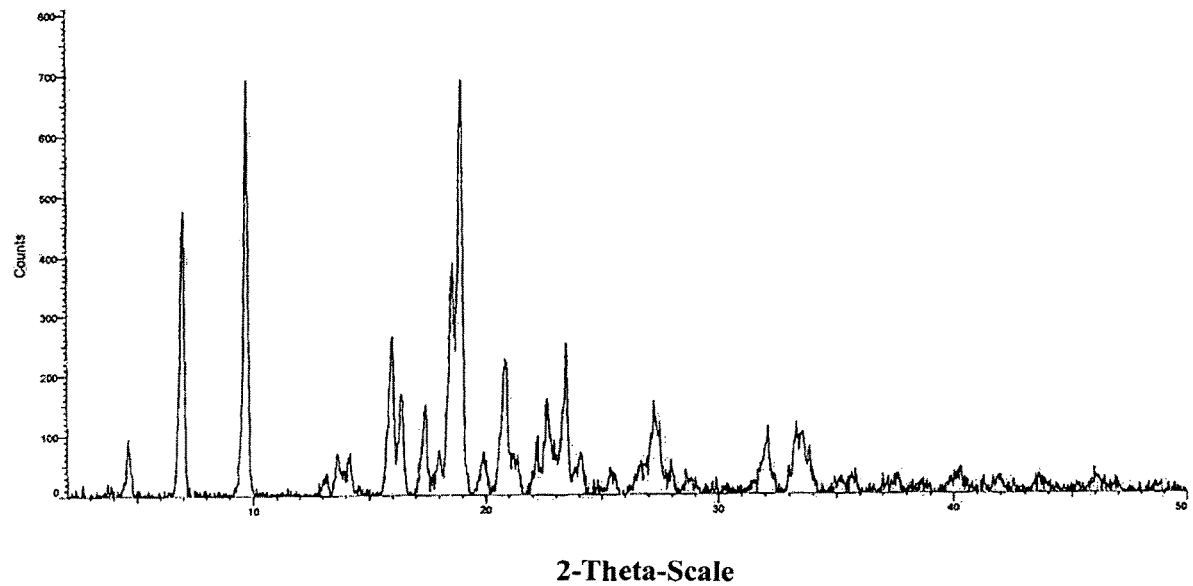
FIG. 5: Illustrates a characteristic PXRD pattern of crystalline Form-II of Empagliflozin-L-proline.

The eighth aspect of the present invention provides crystalline Form-II of Empagliflozin-L-proline. Crystalline Form-II of Empagliflozin-L-proline is characterized by PXRD peaks at about 6.9, 9.7, 18.9 and 20.8±0.2° of two-theta. Crystalline Form-II of Empagliflozin-L-proline is further characterized by PXRD additional peaks at about 4.6, 13.6, 15.9, 16.3, 17.3, 18.6, 19.8, 22.2, 22.6, 23.4, 27.3, 32.0, 33.4±0.2° of two-theta. Crystalline Form-II of Empagliflozin-L-proline is characterized by PXRD pattern as shown in FIG. 5.

Further, the present invention also provides a process for the preparation of crystalline Form-II of Empagliflozin-L-proline, comprising:
- a) suspending Empagliflozin and L-proline in ethanol and toluene;
- b) heating to a suitable temperature;
- c) stirring at suitable temperature;
- d) isolating crystalline Form-II of Empagliflozin-L-proline.

Wherein,

In step-b) & step-c), the suitable temperature is about 60° C. to 65° C.

In step-d), the isolation can be carried out by removing the solvent from the precipitated solid either by filtration or distillation.

Figure 6:
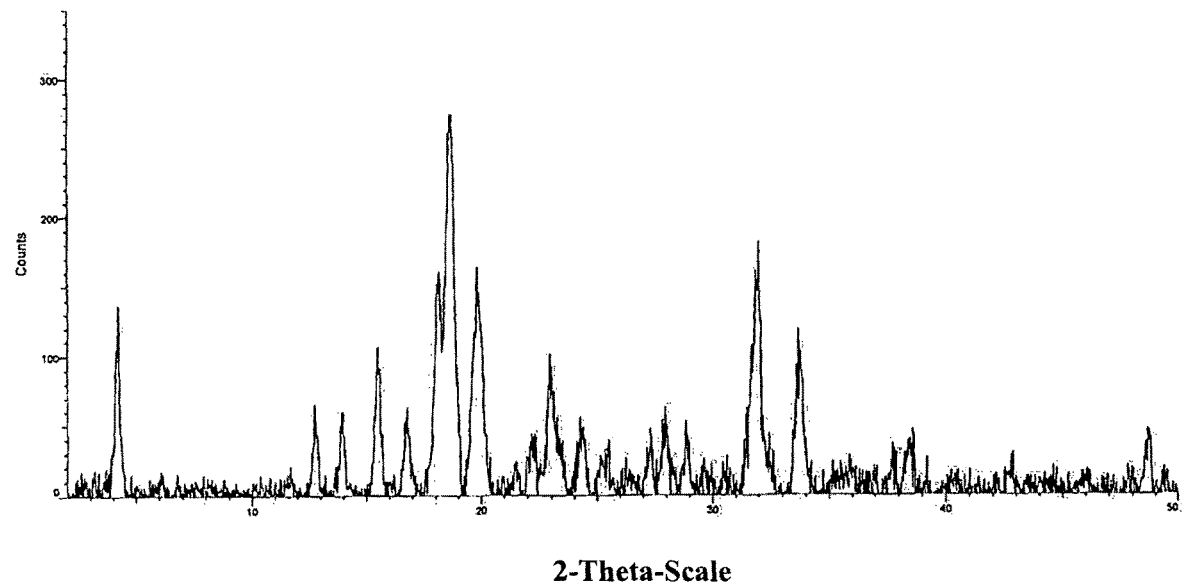
FIG. 6: Illustrates a characteristic PXRD pattern of crystalline Form-III of Empagliflozin-L-proline.

The ninth aspect of the present invention provides crystalline Form-III of Empagliflozin-L-proline. Crystalline Form-III of Empagliflozin-L-proline is characterized by PXRD pattern having peaks at about 4.1, 15.5, 19.8 and 31.9±0.2° of two-theta. Crystalline Form-III of Empagliflozin-L-proline is characterized by PXRD additional peaks at about of 18.2, 18.6, and 33.7±0.2° two-theta. Crystalline Form-III of Empagliflozin-L-proline is characterized by PXRD pattern as shown in FIG. 6.

The present invention also provides a process for the preparation of crystalline Form-III of Empagliflozin-L-proline, comprising:
- a) suspending Empagliflozin and L-proline in a mixture of isopropanol, dichloromethane, chlorobenzene and tetrahydrofuran;
- b) heating to a suitable temperature;
- c) stirring at a suitable temperature;
- d) isolating crystalline Form-III of Empagliflozin-L-proline.

Wherein,

In step-b) & step-c), the suitable temperature is about 60° C. to 65° C.

In step-d), the isolation can be carried out by removing the solvent from the precipitated solid either by filtration or distillation.

Figure 7:
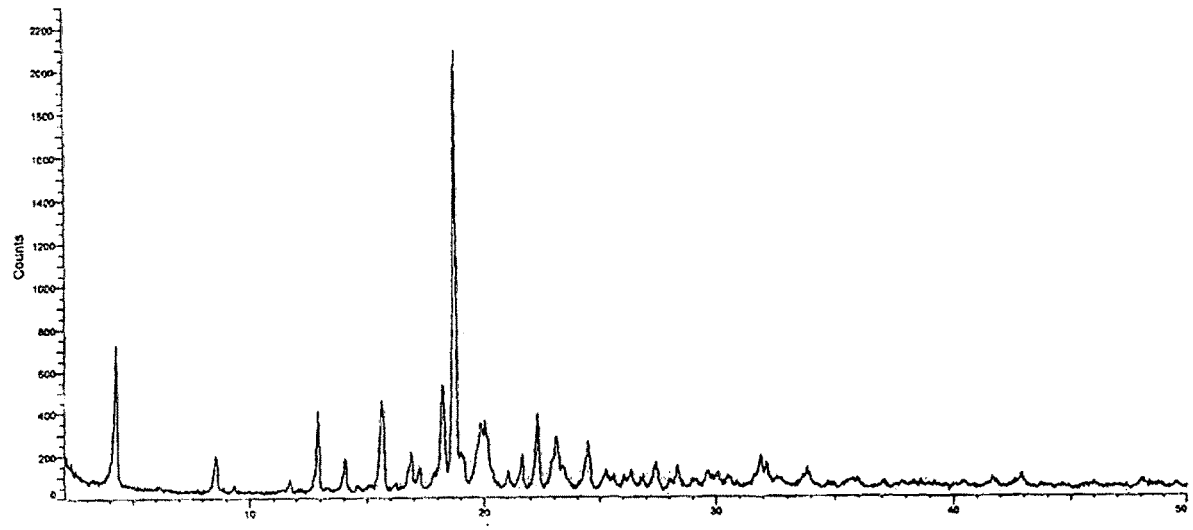
FIG. 7: Illustrates a characteristic PXRD pattern of crystalline Form-IV of Empagliflozin-L-proline.

The tenth aspect of the present invention provides crystalline Form-IV of Empagliflozin-L-proline. Crystalline Form-IV of Empagliflozin-L-proline is characterized by PXRD pattern having peaks at about 4.2, 12.8, 15.6 and 18.7±0.2° of two-theta. Crystalline Form-IV of Empagliflozin-L-proline is further characterized by PXRD additional peaks at about 8.5, 11.6, 14.0, 16.8, 17.1, 18.2, 18.9, 19.9, 21.0, 21.6, 22.2, 23.0, 24.4±0.20 of two-theta. Crystalline Form-IV of Empagliflozin-L-proline is characterized by PXRD pattern as illustrated in FIG. 7.

The present invention also provides a process for the preparation of crystalline Form-IV of Empagliflozin-L-proline, comprising:
- a) suspending Empagliflozin and L-proline in a suitable solvent;
- b) heating to a suitable temperature;
- c) stirring at suitable temperature;
- d) isolating crystalline Form-IV of Empagliflozin-L-proline.

Wherein,

In step-a), the suitable solvent is selected from ethanol, isopropanol, toluene, dichloromethane, chlorobenzene and tetrahydrofuran or mixtures thereof.

In step-b) & step-c), the suitable temperature is about 60° C. to 65° C.

In step-d), the isolation can be carried out by removing the solvent from the precipitated solid either by filtration or distillation.

Figure 8:
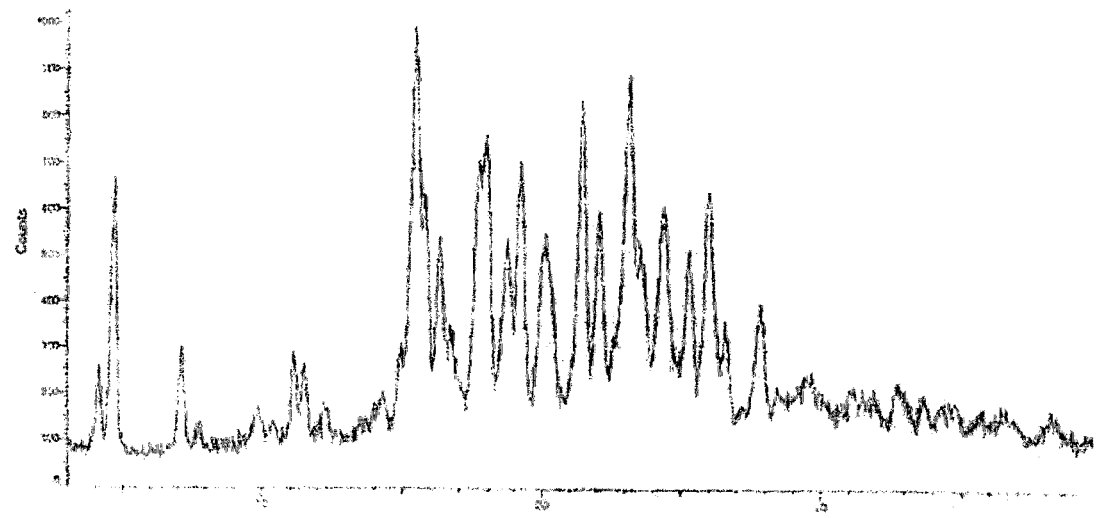
FIG. 8: Illustrates a characteristic PXRD pattern of Empagliflozin N-methyl-2-pyrrolidone solvate

The eleventh aspect of the present invention provides Empagliflozin N-methyl-2-pyrrolidone solvate (NMP solvate). Empagliflozin N-methyl-2-pyrrolidone solvate is characterized by PXRD pattern having peaks at about 4.7, 7.1, 11.1, 23.1, 26.0±0.2° of two-theta. Empagliflozin N-methyl-2-pyrrolidone solvate is characterized by PXRD pattern as illustrated in FIG. 8.

Further, the present invention also provides a process for the preparation of crystalline Empagliflozin N-methyl-2-pyrrolidone solvate, comprising:
- a) Dissolving Empagliflozin in a N-methyl-2-pyrrolidone at a suitable temperature;
- b) adding suitable anti-solvent to the product obtained in step-a) to get crystalline Empagliflozin N-methyl-2-pyrrolidone solvate wherein, in step-b), the suitable anti-solvent is selected from cycloalkanes such as cyclohexane, cyclopentane, cycloheptane and the like; hexane, heptane, tetrahydrofuran, ethyl acetate, methyl tert-butyl ether, ethanol, isopropanol, toluene.

The present invention also provides use of crystalline forms-I to IV, N-methyl-2-pyrrolidone solvate of Empagliflozin in the synthesis of crystalline or amorphous form of Empagliflozin.

Another aspect of the present invention also provides a process for the preparation of Empagliflozin as shown as follows:

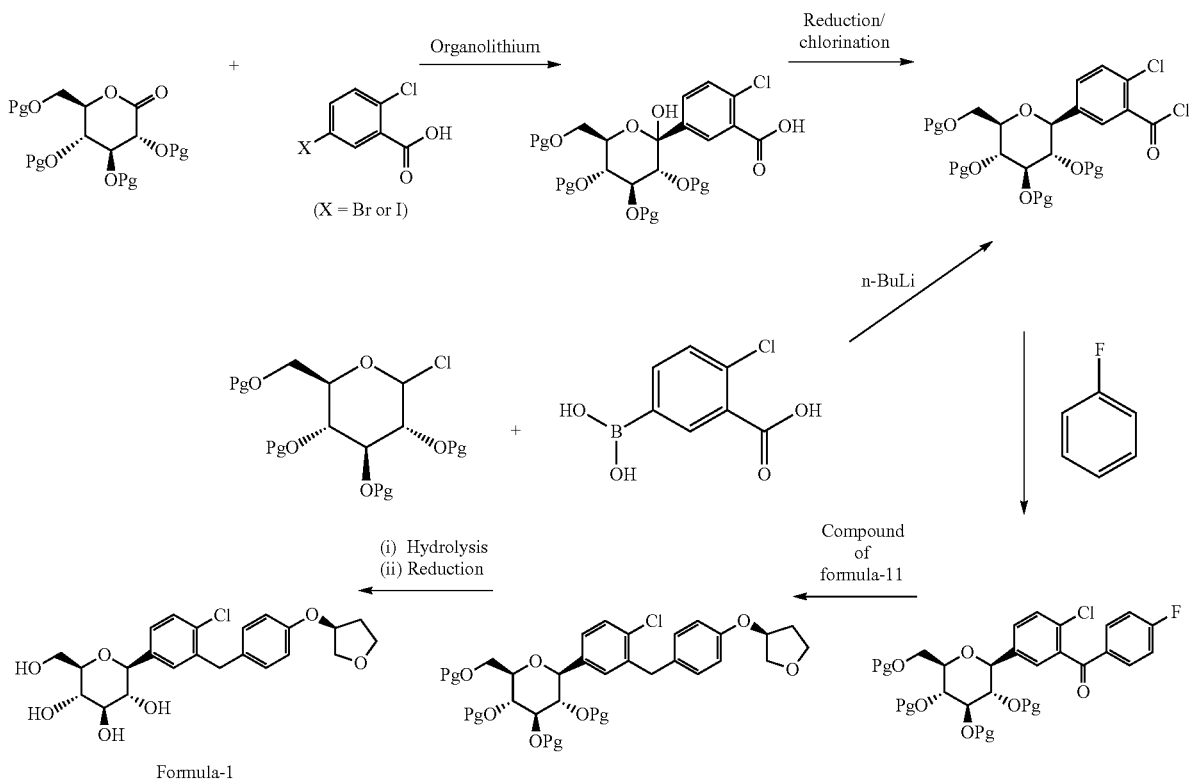

Formula-1 herein, Pg is same as define above.

PXRD analysis of the crystalline form-M, amorphous form, crystalline forms-I to IV of L-proline and N-methyl-2-pyrrolidinone of Empagliflozin were carried out using BRUKER-AXS D8 Advance X-Ray diffractometer using Cu-Ka radiation of wavelength 1.5406 A° and at continuous scan speed of 0.03°/min.

The other aspect of the present invention provides pharmaceutical compositions comprising a therapeutically effective amount of form-M Empagliflozin, Empagliflozin amorphous form, crystalline forms-I to IV of Empagliflozin L-proline, Empagliflozin N-methyl-2-pyrrolidone solvate and one or more pharmaceutically acceptable carriers, excipients or diluents.

Pharmaceutical compositions containing Empagliflozin polymorph form-M, Empagliflozin amorphous form, crystalline forms-I to IV of Empagliflozin L-proline, Empagliflozin N-methyl-2-pyrrolidone solvate of the present invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

The oral pharmaceutical composition may contain one or more additional excipients such as diluents, binders, disintegrants and lubricants. Exemplary diluents include lactose, sucrose, glucose, mannitol, sorbitol, calcium carbonate, microcrystalline cellulose, magnesium stearate and mixtures thereof. Exemplary binders are selected from L-hydroxy propyl cellulose, povidone, hydroxypropyl methyl cellulose, hydroxyethyl cellulose and pre-gelatinized starch.

Exemplary disintegrants are selected from croscarmellose sodium, cros-povidone, sodium starch glycolate and low substituted hydroxylpropyl cellulose.

Exemplary lubricants are selected from sodium stearyl fumarate, magnesium stearate, zinc stearate, calcium stearate, stearic acid, talc, glyceryl behenate and colloidal silicon dioxide. A specific lubricant is selected from magnesium stearate, zinc stearate, calcium stearate and colloidal silicon dioxide.

The compound produced by the present invention can be further micronized or milled by the conventional methods to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

HPLC Method of Analysis:

D-glucitol, 1,5-anhydro-1-C-[4-chloro-3-[[4-[[(3S)-tetrahydro-3-furanyl]oxy]phenyl] methyl]phenyl]-, (1S) compound of formula-1:

Apparatus: A liquid chromatographic system is to be equipped with variable wavelength UV-detector, Column: Symmetry shield RP 18,250×4.6 mm, 5μη (or) equivalent; Flow rate: 1.5 ml/min; Wavelength: 225 nm; Column Temperature: 25° C.; Injection volume: 10μί; Run time: 45 minutes; Diluent: Acetonitrile:water (98:0.2 v/v); Needle wash: Acetonitrile:water (90:10 v/v); Elution: Gradient; Mobile phase-A: Buffer (100%); Mobile phase-B: Acetonitrile:Water:Methanol (80:10:10) v/v; Buffer: 1.6 grams of potassium hydrogen orthophosphate in about 2 gm of 1-Octane sulfonic acid sodium salt anhydrous into 1000 ml of milli-Q-water, then filter this solution through 0.22μ<η>ι nylon membrane filter paper and sonicate to degas it.

The best mode of carrying out the present invention is illustrated by the below mentioned examples. These examples are for illustrative purposes only and in no way limit the embodiments of the present invention.

EXAMPLES

Example-1: Preparation of (5-bromo-2-chlorophenyl)(4-methoxyphenyl)methanone of Formula-2a 5-Bromo-2-chlorobenzoic acid (100 gm) and dichloromethane (500 ml) were charged into a clean and dry RBF at 25-30° C. under nitrogen atmosphere and stirred for 5-10 min. at the same temperature. Dimethylformamide (5 ml) was added to the above formed reaction mixture and cooled to 0-5° C. To this cooled reaction mixture, oxalyl chloride (64.7 gms) was slowly added and stirred for 1 hr at 0-5° C. under nitrogen atmosphere to get benzoyl chloride compound.

Anisole solution (55.0 gms of anisole dissolved in 200 ml of methylene chloride) and AlCl$_3$ (67.8 gms) were added to the above benzoyl chloride compound at 0-5° C. and slowly raised the temperature of the reaction mixture to 25-30° C. with stirred for 6 hours at same temperature. The obtained reaction mixture was quenched with aqueous HCl solution and separated the organic and aqueous layers and extracted the aqueous layer with dichloromethane. The total organic layers were combined and washed with aqueous sodium carbonate solution and distilled off the solvent completely under reduced pressure and followed by co-distilled with isopropanol under reduced pressure to get a solid compound. The obtained solid compound was recrystallized from isopropanol (500 ml) at 70-75° C. and cooled to get the title compound. (Yield: 124.3 g, M.R: 92-97° C.)

Example-2: Preparation of 4-bromo-1-chloro-2-(4-methoxybenzyl)benzene of Formula-3a (5-Bromo-2-chlorophenyl)(4-methoxyphenyl)methanone (100 gms) and methylene dichloride (800 ml) were charged into a clean and dry RBF at 0-5° C. To this reaction mixture, TiCl$_4$ (174.8 gms) and triethylsilylhydride (TESH) (107.6 gms) were slowly added at 0-5° C. and stirred for 15 min. at same temperature. The temperature of the reaction mixture was raise to 25-30° C. and stirred for 4 hrs. at same temperature. Added obtained reaction mixture to chilled water (1000 ml) at 10-15° C. and stirred for 30 min at 25-30° C. Separated the both organic, aqueous layers and extracted the aqueous layer with methylene chloride. The formed total organic layer was washed with 10% aqueous sodium carbonate solution and again with 10% aqueous sodium chloride solution. Distilled off the solvent completely under reduced pressure. Isopropanol (200 ml) and methanol (50 ml) were added to the above distillate and stirred for 30 min at 50-55° C. Cooled the reaction mixture to 0-5° C., filtered and dried the obtained compound to get the title compound. (Yield: 81.26 gms, M.R: 42-47° C.)

Example-3: Preparation of (2S,3R,4S,5S,6R)-2-(4-chloro-3-(4-methoxybenzyl)phenyl)-6-(hydroxymethyl)-2-methoxytetrahydro-2H-pyran-3,4,5-triol 4-Bromo-1-chloro-2-(4-methoxybenzyl)benzene (100 gms) and tetrahydrofuran (1000 ml) were charged into a clean and dry RBF at 25-30° C. To the resulted reaction mixture, (3R, 4S,5R,6R)-3,4,5-tris((trimethylsilyl)oxy)-6-(((trimethylsilyl)oxy)methyl)tetrahydro-2H-pyran-2-one (269 gms) was added at 25-30° C. and cooled to about −75° C. under nitrogen atmosphere and stirred for 20 min. Added N-butyl lithium (410 ml) to the reaction mixture at −75° C. and stirred for 3 hrs at same temperature. A solution of methanesulfonic acid (153.7 gms) in methanol (500 ml) was added to the above reaction mixture at −75° C. and raised the temperature of reaction mixture to 25-30° C. and stirred for 16 hours at same temperature. Basify the obtained reaction mixture with 10% aqueous sodium carbonate solution and washed with n-heptane solvent. Separated the aqueous, organic layers and extracted the aqueous layer twice ethyl acetate. Combined the organic layers and washed with aqueous sodium chloride solution. Distill off the solvent completely from organic layer under reduced pressure to get the title compound. (Yield: 136.0 g)

Example-4: Preparation of (2S,3R,4S,5S,6R)-2-(4-chloro-3-(4-methoxybenzyl)phenyl)-6-(hydroxymethyl)-2-hydroxytetrahydro-2H-pyran-3,4,5-triol of Formula-5a 4-Bromo-1-chloro-2-(4-methoxybenzyl)benzene (100 gms) and tetrahydrofuran (1000 ml) were charged into a clean and dry RBF at 25-30° C. To the resulted reaction mixture, (3R, 4S,5R,6R)-3,4,5-tris((trimethylsilyl)oxy)-6-(((trimethylsilyl)oxy)methyl)tetrahydro-2H-pyran-2-one (269 gms) was added at 25-30° C. and cooled to about −75° C. under nitrogen atmosphere and stirred for 20 min. Added N-butyl lithium (410 ml) to the reaction mixture at −75° C. and stirred for 3 hrs at same temperature. Aqueous HCl (80 ml) and water (720 ml) were added to the above reaction mixture at −75° C. and raised the temperature of reaction mixture to 25-30° C. and stirred for 2 hours at same temperature. Separated the aqueous, organic layers and basify the aqueous layer with 10% aqueous sodium carbonate solution and extracted the aqueous layer twice ethyl acetate. Combined the organic layers and washed with aqueous sodium chloride solution. Distill off the solvent completely from organic layer under reduced pressure to get the title compound. (Yield: 140.0 g, 100%)

Example-5: Preparation of (2S,3R,4R,5S,6R)-2-(4-chloro-3-(4-methoxybenzyl)phenyl)-6-(hydroxymethyl)tetrahydro-2H-pyran-3,4,5-triol of Formula-6a (2S,3R,4S,5S,6R)-2-(4-chloro-3-(4-methoxybenzyl)phenyl)-6-(hydroxymethyl)-2-methoxy tetrahydro-2H-pyran-3,4,5-triol (136 gms), dichloromethane (680 ml) and acetonitrile (680 ml) were charged into a RBF at 25-30° C. and stirred for 15 min to get clear solution. Cooled the reaction mixture to 0-5° C. and added boron trifluoride etherate (144 gms), triethylsilyl hydride (111.5 gms) followed by stirring for 1 hr at same temperature. Basified the obtained reaction mixture with aqueous sodium carbonate solution and stirred for 20 min at 0-5° C. Ethyl acetate (680 ml) was added to the above formed reaction mixture and raised the temperature of the reaction mixture to 25-30° C. and stirred for 15 min at same temperature. Separated the organic, aqueous layers and extracted aqueous layer with ethyl acetate solvent. Combined the total organic layers and washed with aqueous sodium chloride solution. Distilled off the solvent completely from organic layer under reduced pressure to get the title compound. (Yield: 125 gms)

Example-6: Preparation of (2R,3R,4R,5S,6S)-2-(acetoxymethyl)-6-(4-chloro-3-(4-methoxybenzyl) phenyl)tetrahydro-2H-pyran-3,4,5-triyl triacetate of Formula-7a (2S,3R,4R,5S,6R)-2-(4-chloro-3-(4-methoxybenzyl)phenyl)-6-(hydroxymethyl) tetrahydro-2H-pyran-3,4,5-triol (125 gms) dissolved in methylene dichloride (1000 ml) at 25-30° C. Added dimethylaminopyridine (6.6 gms) to the above resulted reaction mixture at 25-30° C. Acetic anhydride (146 gms) was added to the above reaction mixture and stirred for 4 hours at 25-30° C. Diluted the obtained reaction mixture with water and stirred for 30 min. Separated the organic and aqueous layers. Extracted the aqueous layer with methylene dichloride. The total organic layer was washed with aqueous sodium chloride solution, followed by with aqueous sodium carbonate solutions and finally with water. Distilled off the solvent completely from the organic layer under reduced pressure and co-distilled with methanol under reduced pressure. Added methanol (500 ml) to the above distillate and stirred for 1 hr at 70° C. Cooled the reaction mixture to 0-5° C. and stirred for 2 hrs at same temperature. Filtered the obtained compound and washed with methanol solvent and dried to get the title compound. (Yield: 80 gms)

Example-7: Preparation of the (2R, 3R, 4R, 5S, 6S)-2-(acetoxymethyl)-6-(4-chloro-3-(4-hydroxybenzyl)phenyl)tetrahydro-2H-pyran-3,4,5-triyl triacetate of Formula-8a Aluminum chloride (94.85 gm) and dichloromethane (200 ml) were charged into a round bottom flask. Dodecanethiol (143 gms) was added to the above resulted solution at 25-30° C. and cooled the reaction mixture to 15-20° C. To this reaction mixture, a solution of (2R,3R,4R,5S,6S)-2-(acetoxymethyl)-6-(4-chloro-3-(4-methoxybenzyl)phenyl)tetrahydro-2H-pyran-3,4,5-triyl triacetate (100 gms dissolved in 200 ml of dichloromethane) added at 15-20° C. and stirred for 3 hrs at 25-30° C. Chilled water (1000 ml) added to the above reaction mixture and stirred for about 15 mins at 25-30° C. Separated the organic and aqueous layers. The aqueous layer was extracted with dichloromethane. The total organic layer was washed with aqueous sodium carbonate solution and again washed with water. Distilled off the solvent completely from the organic layer under reduced pressure. The obtained compound was co-distilled with cyclohexane (100 ml). Cyclohexane (600 ml) was added to the above distillate and heated to 45-50° C. and stirred for 45 min. at same temperature. Cooled the reaction mixture to 25-30° C. and stirred for 2 hrs. Filtered, washed the resulting compound with cyclohexane and dried to get the title compound. (Yield: 86.0 gms)

Example-8: Preparation of the (2R, 3R, 4R, 5S, 6S)-2-(acetoxymethyl)-6-(4-chloro-3-(4-hydroxybenzyl) phenyl)tetrahydro-2H-pyran-3,4,5-triyl triacetate of Formula-8a Aluminum chloride (25.8 gm) was dissolved in dichloromethane (75 ml) in a round bottom flask. Dodecanethiol (125 gms) was added to the above reaction solution at 25-30° C. To this reaction mixture, 25 gms of (2R,3R,4R, 5S,6S)-2-(acetoxymethyl)-6-(4-chloro-3-(4-ethoxybenzyl) phenyl)tetrahydro-2H-pyran-3,4,5-triyl triacetate (dissolved in 50 ml of dichloromethane) was slowly added for 15-30 mins at 25-30° C. and stirred for 2-3 hours at the same temperature. Water (250 ml) was added to the above reaction mass and stirred for about 10-15 mins. Obtained organic and aqueous layers were separated and organic layer was washed with water. Distilled off the solvent completely from the organic layer under reduced pressure. The obtained compound was co-distilled with cyclohexane (75 ml). Cyclohexane (375 ml) was added to the obtained distillate at 40-50° C. and cooled the reaction mixture to 25-30° C. with stirred for 1-2 hours. Filtered the obtained compound and washed with cyclohexane. The obtained compound was dried to get the title compound.
Yield: 20.0 gms (91.11%)

Example-9: Preparation of (R)-tetrahydrofuran-3-yl 4-nitrobenzenesulfonate (R)-3-Hydroxyfuran (100 gms) and dichloromethane (1000 ml) were charged into a clean and dry RBF at 25-30° C. and stirred for 10 min at same temperature. To the resulted reaction mixture, dimethylaminopyridine (11.8 gms) and triethylamine (229 gms) were added and cooled to 0-5° C. p-Nitro benzenesulfonyl chloride (301.0 gms) was added to the above reaction mixture and raised the temperature to 25-30° C. and stirred for 4 hrs at same temperature. Water (500 ml) was added to the above reaction mixture and stirred for 20 min. and separate the aqueous and organic layers. The organic layer was washed with aqueous hydrochloride solution and followed by with aqueous sodium bicarbonate. Distilled the solvent completely from the solution. Co-distilled the obtained compound with methanol. The obtained compound was dissolved in methanol (500 ml) at 60-65° C. and stirred for 1 hr. Cooled the reaction mixture to 0-5° C. and again stirred for 2 hrs. Filtered, washed and dried obtained material to get the title compound as a solid. (Yield: 280.0 gms).

Example-10: Preparation of (2R,3R,4R,5S,6S)-2-(acetoxymethyl)-6-(4-chloro-3-(4-(((S)-tetrahydrofuran-3-yl)oxy)benzyl)phenyl)tetrahydro-2H-pyran-3,4,5-trityl triacetate of Formula-9a (2R,3R,4R,5S,6S)-2-(acetoxymethyl)-6-(4-chloro-3-(4-hydroxybenzyl)phenyl)tetra hydro-2H-pyran-3,4,5-triyl triacetate (100 gms) was dissolved in acetonitrile (1000 ml) at 25-30° C. To this reaction mixture, (R)-tetrahydrofuran-3-yl 4-nitrobenzenesulfonate (54.75 gms), potassium carbonate (125.88 gms) were added and heated the reaction mixture to 80° C. and stirred for 8 hrs. Filtered the reaction mixture and washed with acetonitrile and distilled off the solvent completely under reduced pressure. Added dichloromethane (600 ml), dimethylaminopyridine (2.22 gms), aceticanhydride (37.16 gms) to the above obtained compound and stirred for 3 hrs at 25-30° C. Diluted the reaction mixture with water (500 ml) and again stirred for 15 min. The aqueous layer was extracted with dichloromethane. The organic layers were combined and washed with aqueous hydrochloride solution. The organic layer was washed with aqueous sodium carbonate solution and followed by again washed with water. Distilled off the solvent completely from the solution under reduced pressure. Methanol (400 ml) was added to the above distillate and heated to 65° C. and stirred for 1 hr at same temperature to get the clear solution. Cooled the reaction mixture to 25-30° C. and further cooled to 0-5° C. stirred for 2 hrs at same temperature. Filtered, washed the obtained compound with methanol and dried to get the title compound. (Yield: 95.8 gins, M.R: 150-155° C.)

Example-11: Preparation of D-glucitol, 1,5-anhydro-1-C-[4-chloro-3-([[4-[[((3S)-tetrahydro-3furanyl]oxy]phenyl]methyl]phenyl]-, (1S) (Empagliflozin (Formula-1))

The product of example-10 (100 gms) and methanol (800 ml) were charged into a RBF at 25-30° C. Added aqueous sodium hydroxide solution (154 gms dissolved in 100 ml of water) to the resulted reaction mixture and raised reaction mixture temperature to 65° C. and stirred for 20 hrs at same temperature. Filter the formed reaction mixture with methanol Cooled the reaction mixture to 25-30° C. and added water (1000 ml), ethyl acetate (1000 ml). Raised the reaction mixture temperature to 45-50° C. and stirred for 45 mins at same temperature. Organic and aqueous layers were separated and distilled off the solvent completely from the organic layer under reduced pressure. Filtered and dried the obtained material to get the title compound. (Yield: 56.5 gins, MR: 147-150° C.).

Example-12: Preparation of D-glucitol, 1,5-anhydro-1-C-[4-chloro-3-[[4-[[(3S)-tetrahydro-3-furanyl]oxy]phenyl]methyl]phenyl]-, (1S) (Empagliflozin (Formula-1))

The product of example 10 (10 gms) was dissolved in dimethyl formamide (100 ml) at 25-30° C. To this reaction mixture, cesium carbonate (15.37 gms) and tetrahydrofuran-3-yl 4-nitrobenzenesulfonate (R-isomer) (6.62 gms) were added and raised the reaction mixture temperature to 50-60° C. and stirred for 5 to 6 hrs. Cooled the reaction mixture to 25-30° C.

To the above obtained reaction mixture, aqueous sodium hydroxide solution (2.4 gms of sodium hydroxide dissolved in 20 ml of water) was added at 25-30° C. and heated the reaction mixture to 50-60° C. and stirred for 5 to 6 hours at same temperature. Cooled the reaction mixture to 25-30° C. To the cooled reaction mixture, water (100 ml) and ethyl acetate (100 ml) were added and stirred for 10-15 mins. Organic and aqueous layers were separated and distilled off the solvent completely from the organic layer under reduced pressure. Obtained compound was dissolved in ethyl acetate (40 ml), methanol (10 ml) at 40-45° C. and cooled to 0-5° C. and stirred for 1-2 hours. Filtered and washed with ethyl acetate and dried the material to get the title compound. Yield: 3.0 gms (38%), MR: 147-150° C.

Example-13: Preparation of (R)-tetrahydrofuran-3-yl 4-nitrobenzenesulfonate (S)-Tetrahydrofuran (10 gms) was dissolved in tetrahydrofuran (100 ml) at 25-30° C. Cooled the reaction mixture to 0-5° C., added triphenylphosphine (44.65 gms), p-nitrobenzoic acid (18.96 gms) and stirred for 30 min at the same temperature. Diisopropyl azodicarboxylate (DIAD) (27.53 gms) was slowly added to the above reaction mixture at 0-5° C. and stirred for 60 min at the same temperature. Distilled off the solvent completely from reaction mixture under reduced pressure at 45-50° C. Methanol (100 ml) was added to the above obtained distillate and stirred for 15 min at 0-5° C. and $K_2CO_3$ (31.32 gms) was added to the reaction mixture and stirred for 30 min. Filtered the reaction mixture and washed with methanol. Distilled off the solvent completely from the filtrate under reduced pressure and cooled to 25-30° C. Add water (10 ml) to the above obtained solid at 25-30° C. and stirred for 45 min. at the same temperature. Mixture of methylene chloride (50 ml) and cyclohexane (50 ml) was added to the above reaction mixture and stirred for 25 min. at the same temperature. Separated the organic and aqueous layers. Mixture of methylene chloride (50 ml) and cyclohexane (50 ml) was added to the aqueous layer and separated organic and aqueous layers. Distilled off the total aqueous layer under reduced pressure at below 75-80° C. and co-distillated with methylene chloride (20 ml). Add methylene chloride (100 ml) to the above distillate and cooled to 0-5° C. Triethylamine (22.97 gms) was added to the reaction mixture at 0-5° C. and stirred for 25 min at same temperature. p-Nitrobenzene sulfonyl chloride (25.15 gins) and dimethylaminopyridine (1.38 gins) were added to the reaction mixture at 0-5° C. and stirred for 2 hrs at same temperature. Water was added to the reaction mixture with and separated the organic and aqueous layers. Organic layer was washed with aqueous HCl solution followed by aqueous $Na_2CO_3$ solution, water and finally with aqueous sodium chloride solution consecutively at 25-30° C. Distilled off the solvent from the reaction mixture at 40° C. and co-distilled with methanol (30 ml). Add methanol (10 ml) to the above obtained compound at 25-30° C. Heated the reaction mixture to 60-65° C. and stirred for 45 min at same temperature. Cooled the reaction mixture to 0-5° C. and stirred for 45 min. at same temperature. Filtered the precipitated solid and washed with methanol solvent. Dried the obtained material at 45-50° for 4-5 hrs to get the title compound. (Yield: 6.0 gms, Purity by HPLC: 99.93%)

Example-14: Preparation of (((2S,3S,4R,5R,6R)-2-(4-chloro-3-(4-((trimethylsilyl)oxy)benzyl)phenyl)-6-(((trimethylsilyl)oxy)methyl)tetrahydro-2H-pyran-3,4,5-triyl)tris(oxy))tris(trimethylsilane) of formula-14a Add (2S,3R,4R,5S,6R)-2-(4-chloro-3-(4-hydroxybenzyl) phenyl)-6-(hydroxymethyl) tetrahydro-2H-pyran-3,4,5-triol (10 gms) to tetrahydrofuran (100 ml) at 25-30° C. and stirred for 10 min. at the same temperature. N-Methylmorpholine (15.99/17.57 gr/ml, 6 moles) was added to the above reaction mixture and cooled to 0-5° C. and added trimethylchlorosilane (11.40/1342 gms/ml, 4 moles) at same temperature. Heated the reaction mixture to 45-50° C. and stirred for 10-11 hrs at the same temperature. Cooled the reaction mixture temperature to 0-5° C. and quenched with chilled water. Ethyl acetate (500 ml) was added to the reaction mixture and separate the organic and aqueous layers. Extract the aqueous layer using ethyl acetate. Combined the organic layers followed by washed with 10% sodium dihydrogen phosphate dehydrate $(NaH_2PO_4).2H_2O$ and then with 10% NaCl solution successively and dried over sodium sulfate. Distilled off the solvent completely from the organic layer under reduced pressure to get the title compound. (Yield: 17.8 gms)

Example-15: Preparation of D-glucitol, 1,5-anhydro-1-C-[4-chloro-3-[[4-[[(3S)-tetrahydro-3-furanyl]oxy]phenyl]methyl]phenyl]-, (1S) (Empagliflozin (Formula-1))

Add (((2S,3S,4R,5R,6R)-2-(4-chloro-3-(4-((trimethylsilyl)oxy)benzyl)phenyl)-6-(((trimethylsilyl)oxy)methyl)tetrahydro-2H-pyran-3,4,5-triyl)tris(oxy))tris(trimethylsilane) (72 gms) to acetonitrile (720 ml) at 25-30° C. and stirred for 10 min. at the same temperature. (R)-Tetrahydrofuran-3-yl 4-nitrobenzenesulfonate (15.9 gms) and $K_2CO_3$ (67.0 gms) were added to the reaction mixture at 25-30° C. and stirred for 10 min. Heated the reaction mixture to 75-80° C. and stirred for 10-11 hrs at same temperature. Filtered the reaction mixture and washed with acetonitrile. Add water (216 ml), 10% aqueous HCl, acetonitrile (360 ml) to the filtrate and separated the organic and aqueous layers. Extracted the aqueous layer using ethyl acetate. Basify the organic layer with 10% $Na_2CO_3$ solution and separated the organic and aqueous layers. Extracted the aqueous layer using ethyl acetate. Distilled off the solvent completely from the organic layer under reduced pressure. Add ethyl acetate (72 ml) to the above obtained compound at 55-60° C. and stirred for 90 min at 25-30°. Filtered the solid compound and washed with ethyl acetate followed by dried under reduce pressure to get the title compound. (Yield: 9.4 gms).

Example-16: Preparation of D-glucitol, 1,5-anhydro-1-C-[4-chloro-3-[[4-[[(3S)-tetrahydro-3-furanyl]oxy]phenyl]methyl]phenyl]-, (15S) (Empagliflozin (Formula-1))

Add 4-(2-chloro-5-((2S,3S,4R,5R,6R)-3,4,5-tris((trimethylsilyl)oxy)-6-(((trimethylsilyl)oxy)methyl)tetrahydro-2H-pyran-2-yl)benzyl)phenol (17 gms) to acetonitrile (170 ml) at 25-30° C. and stirred to 10 min. at the same temperature. (R)-Tetrahydrofuran-3-yl 4-nitrobenzenesulfonate (4.2 gms) and $K_2CO_3$ (17.5 gms) were added to the reaction mixture at 25-30° C. Heated the reaction mixture to 75-80° C. and stirred for 9-10 hrs at the same temperature. Cooled the reaction mixture to 55-60° C. and stirred for 3 hrs at same temperate. Filtered the reaction mixture and washed with hot acetonitrile. Distilled off the solvent from the filtrate under reduced pressure. Add water (51 ml), 10% aqueous HCl, ethyl acetate (85 ml) to the distillate and separated the organic and aqueous layers. Extracted the aqueous layer using ethyl acetate. Basify the organic layer with 10% $Na_2CO_3$ solution and separated the organic and aqueous layers. Extracted the aqueous layer using ethyl acetate. Distilled off the solvent completely from the organic layer under reduced pressure. Add ethyl acetate (72 ml) to the above obtained compound at 55-60° C. and stirred for 90 min at 25-30°. Filtered the solid compound and washed with ethyl acetate followed by dried under reduce pressure to get the title compound. (Yield: 2 gms).

Example-17: Preparation of Crystalline Form-M of Empagliflozin of Formula-1

Empagliflozin (500 mg) and ethyl acetate (40 ml) were charged into a clean and dry RBF at 25-30° C. Raised the resulting reaction mixture temperature to 85° C. and stirred for 15 min at same temperature. The obtained reaction mixture was added to chilled n-heptane solution (60 ml) at −55° C. and stirred for 10 min at same temperature. Filtered the obtained material and dried to get the title compound. (Yield: 420 mg).
The obtained crystalline solid Form-M is characterized by PXRD having peaks at about 15.0, 18.1, 19.1, 22.5±0.2 degrees of two-theta as illustrated in FIG. 1.

Example-18: Preparation of Amorphous Form of Empagliflozin

Figure 2:
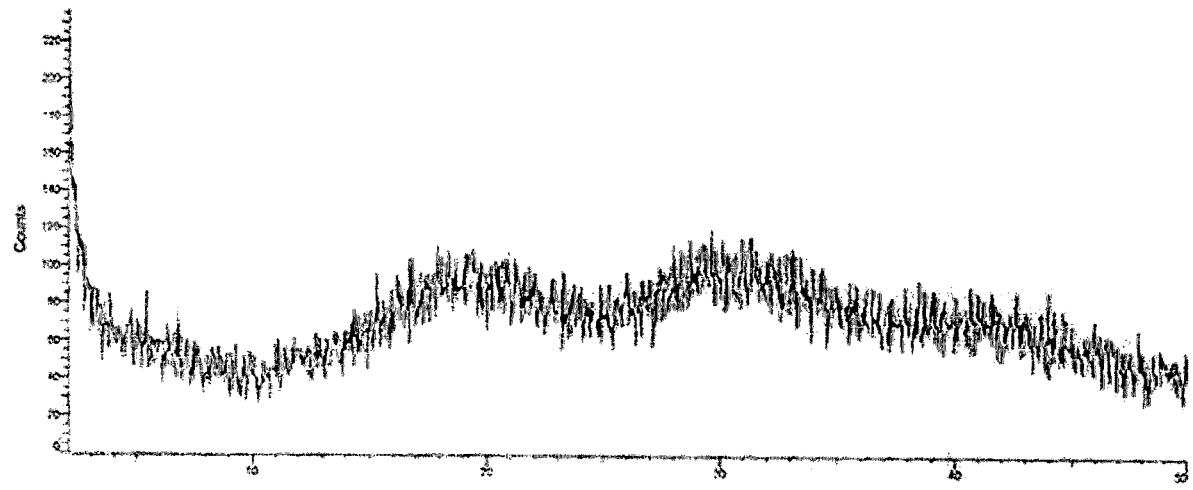
FIG. 2: Illustrates a characteristic PXRD pattern of amorphous form of Empagliflozin according to examples 14 and 15.

Empagliflozin (500 mg) and acetone (10 ml) were charged into a clean and dry RBF at 25-30° C. Raised the resulting reaction mixture temperature to 50° C. and stirred for 5 min at the same temperature. Filtered the resulting reaction mixture and the filtrate was taken into a clean and dry Buchi funnel and distilled off the solvent completely under reduced pressure followed by dried to afford the amorphous form of Empagliflozin. (Yield: 420 mg). (D90 is 189.4 μm, D50 is 70.6 μm, D10 is 17.0 μm and D(3,2) is 34.6 μm and D(4,3) is 90.3 μm) The obtained amorphous form is characterized by PXRD pattern as illustrated in FIG. 2.

Example-19: Preparation of Amorphous Form of Empagliflozin

Empagliflozin (500 mg) and ethyl acetate (10 ml) were charged into a clean and dry RBF at 25-30° C. Raised the reaction mixture temperature to 75-80° C. and stirred for 5 min at same temperature. Filtered the resulting reaction mixture and filtrate was taken into clean and dry Buchi funnel and distilled off the solvent completely under reduced pressure and dried to afford the amorphous form of Empagliflozin. (Yield: 390 mg).
The PXRD pattern of above obtained compound is similar to FIG. 2.

Example-20: Preparation of Solid Dispersion of Empagliflozin

Figure 3:
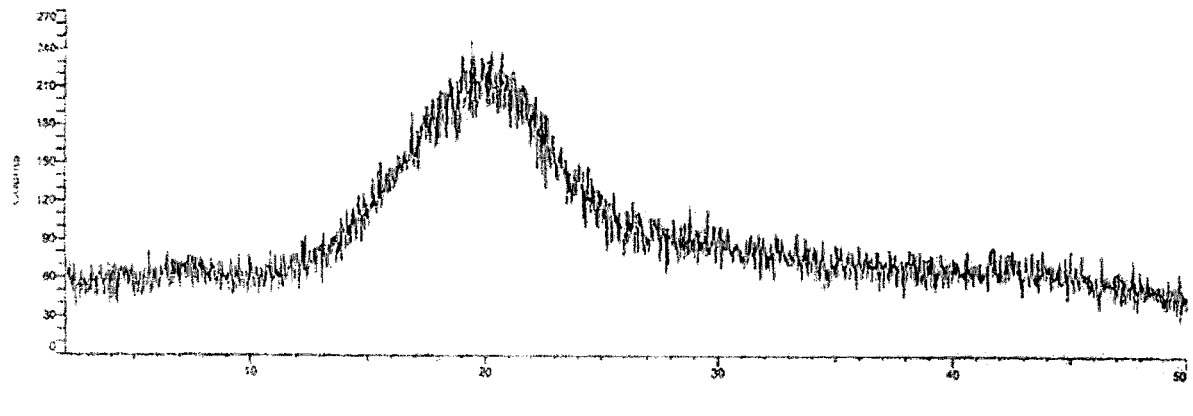
FIG. 3: Illustrates a characteristic PXRD pattern of solid dispersion of Empagliflozin according to examples 16 and 17.

Empagliflozin (500 mg) and methanol (30 ml) were charged into a clean and dry RBF at 25-30° C. and stirred for 5 min at same temperature. Hydroxy propyl cellulose (HPC) (500 mg) and dichloromethane (30 ml) were charged into another clean and dry round bottom flask at 25-30° C. and stirred for 10 min at same temperature. The resulted reaction solution was added to the above methanolic Empagliflozin and stirred for 15 min at 60° C. Distilled off the solvent completely from the reaction mixture under the reduced pressure and dried the material to get the title compound (Yield: 380 mg).
The obtained amorphous compound was characterized by PXRD pattern as illustrated in FIG. 3.

Example-21: Preparation of Solid Dispersion of Empagliflozin

Empagliflozin (500 mg) and methanol (30 ml) were charged into a clean and dry RBF at 25-30° C. and stirred for 5 min at same temperature to get the clear solution. Crosspovidone and dichloromethane (30 ml) were charged into another clean and dry round bottom flask at 25-30° C. and stirred for 10 min at same temperature to get the clear solution. The resulted solution was added to the above Empagliflozin solution at 60° C. and stirred for 15 min at same temperature. Distilled off the solvent completely from the reaction mixture under reduced pressure and dried the material to get the title compound (Yield: 320 mg).
The obtained compound was characterized by PXRD pattern as illustrated in FIG. 3.

Example-22: Preparation of Crystalline Form-I of Empagliflozin-L-Proline

Empagliflozin (500 mg) and L-proline (20 mg), isopropanol (5 ml), dichloromethane (5 ml), chlorobenzene (5 ml) and tetrahydrofuran (5 ml) mixture were charged into a clean and dry RBF at 25-30° C. Raised the resulting reaction mixture temperature to 60-65° C. and stirred for 60 min at same temperature. Slowly cooled the reaction mixture to 25-30° C. and stirred for 5 hrs at same temperature. Filtered the obtained precipitated solid and dried to get the title compound (Yield: 380 mg).

The obtained crystalline Form-I of Empagliflozin-L-proline is characterized by PXRD having peaks at about 4.2, 15.6, 18.7, 19.9, 22.3, 31.9, 33.8±0.2 degrees of two-theta as illustrated in FIG. 4.

Example-23: Preparation of Crystalline Form-II of Empagliflozin-L-Proline

Empagliflozin (2 gr) and L-proline (50 mg), ethanol (20 ml) and toluene (20 ml) were charged into a clean and dry RBF at 25-30° C. Heating the resulting reaction mixture temperature to 60-65° C. and stirred for 7 hrs at same temperature. Filtered the obtained precipitated solid and dried to get the title compound (Yield: 1.4 gr).
The obtained of crystalline Form-II of Empagliflozin-L-proline is characterized by PXRD having peaks at about 4.6, 6.9, 9.7, 13.6, 15.9, 16.3, 17.3, 18.6, 18.9, 19.8, 20.8, 22.2, 22.6, 23.4, 27.3, 32.0, 33.4±0.2 degrees of two-theta as illustrated in FIG. 5

Example-24: Preparation of Crystalline Form-III of Empagliflozin-L-Proline

Empagliflozin (2 gr) and L-proline (50 mg), isopropanol (5 ml) and dichloromethane (5 ml), chlorobenzene (5 ml) and tetrahydrofuran (5 ml) were charged into a clean and dry RBF at 25-30° C. Raised the resulting reaction mixture temperature to 60-65° C. and stirred for 7 hrs at same temperature. Filtered the obtained precipitated solid and dried to get the title compound (Yield: 670 mg).
The obtained of crystalline Form-III of Empagliflozin-L-proline is characterized by PXRD having peaks at about 4.1, 15.5, 18.2, 18.6, 19.8, 23.0, 31.9 and 33.7 f 0.2° of 2 theta as illustrated in FIG. 6.

Example-25: Preparation of Crystalline Form-IV of Empagliflozin-L-Proline

Empagliflozin (500 mg) and L-proline (100 mg), ethanol (10 ml) and toluene (10 ml) were charged into a clean and dry RBF at 25-30° C. Raised the resulting reaction mixture temperature to 60° C. and stirred for 8 hrs at same temperature. Filtered the obtained precipitated solid and dried to get the title compound (Yield: 420 mg).
The obtained of crystalline Form-IV of Empagliflozin-L-proline is characterized by PXRD having peaks at about 4.2, 8.5, 11.6, 12.8, 14.0, 15.6, 16.8, 17.1, 18.2, 18.7, 18.9, 19.9, 21.0, 21.6, 22.2, 23.0, 24.4±0.2 degrees of two-theta as illustrated in FIG. 7

Example-26: Preparation of Crystalline Form-IV of Empagliflozin-L-Proline

Empagliflozin (500 mg) and L-proline (100 mg), isopropanol (5 ml), dichloromethane (5 ml), chlorobenzene (5 ml) and tetrahydrofuran (5 mil) were charged into a clean and dry RBF at 25-30° C. Raised the resulting reaction mixture temperature to 60° C. and stirred for 8 hrs at same temperature. Filtered the obtained precipitated solid and dried to get the title compound (Yield: 380 mg).
The obtained crystalline Form-IV of Empagliflozin-L-proline is characterized by PXRD pattern as illustrated in FIG. 7.

Example-27: Preparation of Empagliflozin N-Methyl-2-Pyrrolidone Solvate

Empagliflozin (5 gr) and N-methyl-2-pyrrolidone (25 ml) were charged into a clean and dry RBF at 25-30° C. Heated the reaction mixture to 55-60° C. Add above clear solution to chilled cyclohexane (1000 ml) in another round bottom flask at 0-5° C. and stirred for 3 hrs at same temperature. Filtered the precipitated solid under reduced pressure to get the title compound. (Yield: 4.5 gms)
The obtained Empagliflozin N-methyl-2-pyrrolidone solvate is characterized by PXRD pattern as illustrated in FIG. 8.

Example-28: Preparation of Empagliflozin N-Methyl-2-Pyrrolidone Solvate

Empagliflozin (10 gr) and N-methyl-2-pyrrolidone (30 ml) were charged into a clean and dry RBF at 25-30° C. Heated the reaction mixture to 55-60° C. Add cyclohexane (1000 ml) to the above reaction mixture at 0-5° C. and stirred for 2-3 hrs at same temperature. Filtered the precipitated solid under reduced pressure to get the title compound. (Yield: 9.8 gms)
The PXRD pattern of obtained Empagliflozin N-methyl-2-pyrrolidone solvate is similar to FIG. 8.

The invention claimed is:
1. A process for the preparation of D-glucitol, 1,5-anhydro-1-C-[4-chloro-3-[[4-[[(3S)-tetrahydro-3-furanyl]oxy]phenyl]methyl] phenyl]-, (1S) of formula-1

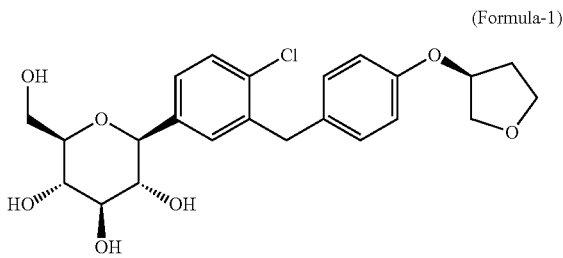 [SMILES: OC[C@H]1O[C@@H](c2ccc(Cl)c(Cc3ccc(O[C@H]4CCOC4)cc3)c2)[C@H](O)[C@@H](O)[C@@H]1O]

(Formula-1)

comprising:
a) reacting the compound of general formula-7 with suitable thiol reagent in presence of suitable Lewis acid in a suitable solvent to get the compound of general formula-8;

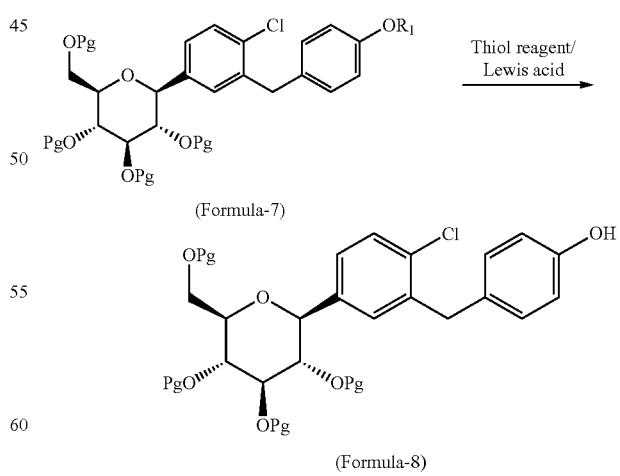

b) reacting the compound of general formula-8 with the compound of general formula-11 in presence of a suitable base in a suitable solvent to provide the compound of general formula-9;

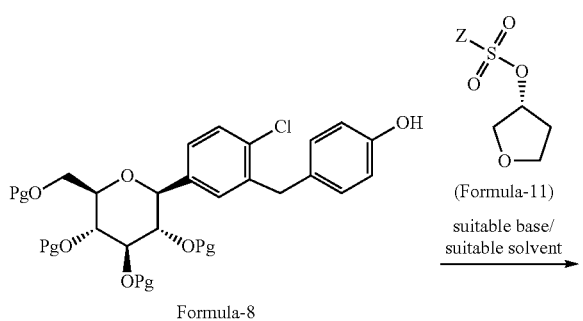

Formula-8

(Formula-11)

suitable base/
suitable solvent
→

Formula-9 wherein, $R_1$ is selected from $C_1$-$C_5$ straight or branched chain alkyl groups; Pg is selected from —C(O)O$C_1$-$C_6$ alkyl; optionally substituted —C(O)O$C_1$-$C_6$ aryl; optionally substituted —$C_1$-$C_{12}$ aryl($C_1$-$C_3$)alkyl; optionally substituted $C_7$-$C_{11}$ aryl carbonyl; $C_1$-$C_6$ alkanoyl; $C_1$-$C_6$ alkylsulfonyl; Z is alkyl group having 1-4 carbons or aryl group substituted with one or more electron withdrawing groups; and c) converting the compound of general formula-9 to compound of formula-1.

2. The process of claim 1, wherein in step-a) the suitable thiol reagent is thiol or dithiol alcohol which is selected from the group consisting of decanethiol, dodecane thiol, cyclohexane thiol, cyclopentane thiol, cyclo butane thiol, thiophenol, methanethiol, ethanethiol, 1-propanethiol, 2-propanethiol, n-butanethiol, tert-butanthiol, furan-2-ylmethanethiol, ethandithiol, 1,2-propanedithiol, 1,3-propanedithiol, 1,3-butanedithiol, 1,4-butanedithiol; the suitable Lewis acid is selected from the group consisting of AlCl$_3$, AlBr$_3$, BCl$_3$, TiCl$_4$, FeCl$_3$ and ZnCl$_2$.

3. The process of claim 1, wherein in step-b) the suitable base is "alkali metal hydroxides" selected from the group consisting of lithium hydroxide, sodium hydroxide, potassium hydroxide; "alkali metal carbonates" selected from the group consisting of sodium carbonate, potassium carbonate, lithium carbonate; "alkali metal bicarbonates" selected from the group consisting of sodium bicarbonate, potassium bicarbonate, lithium bicarbonate; "alkali metal hydrides" selected from the group consisting of sodium hydride, potassium hydride, lithium hydride; "alkali metal alkoxides" selected from the group consisting of sodium methoxide, sodium ethoxide, sodium tert-butoxide, potassium methoxide, potassium ethoxide, potassium tert-butoxide.

4. The process of claim 1, wherein in step-a) and step-b), the suitable solvent is alcohol solvents selected from the group consisting of methanol, ethanol, n-propanol, i-propanol, butanol; chloro solvents selected from the group consisting of methylene chloride, chloroform, carbon tetrachloride; ketone solvents selected from the group consisting of acetone, butanone; nitrile solvents selected from the group consisting of acetonitrile, propionitrile, butyronitrile; ester solvents selected from the group consisting of ethyl acetate, methyl acetate, butyl acetate; hydrocarbon solvents selected from the group consisting of heptane, hexane, benzene, toluene, xylene; ether solvents selected from the group consisting of diethyl ether, methyl tert-butyl ether, tetrahydrofuran, 1,4-diethyl ether or mixture thereof.

5. The process of claim 1, comprising the process comprising:

a) reacting compound of formula-7a with dodecanethiol/ AlCl$_3$ to provide compound of formula-8a;

(Formula-7a)

Dodecanethiol/
AlCl$_3$
→

(Formula-8a)

b) reacting compound of formula-8a with (R)-tetrahydrofuran-3-yl 4-nitrobenzenesulfonate in presence of K$_2$CO$_3$/dimethylformamide to provide compound of formula-9a; and (Formula-8a)

(R)-Tetrahydrofuran-3-yl 4-nitro benzenesulfonate/
K$_2$CO$_3$/dimethylformamide
→

-continued

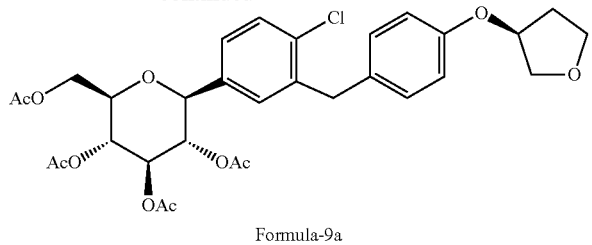

Formula-9a c) deprotecting the compound of formula-9a to provide the compound of formula-1.

6. A process for the preparation of compound of general formula-8,

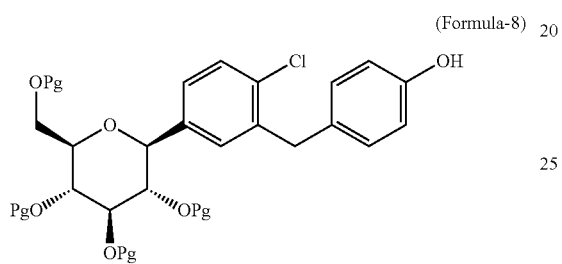
(Formula-8)

comprising reacting the compound of general formula-7 with thiol reagent in presence of catalyst in a suitable solvent to provide compound of formula-8

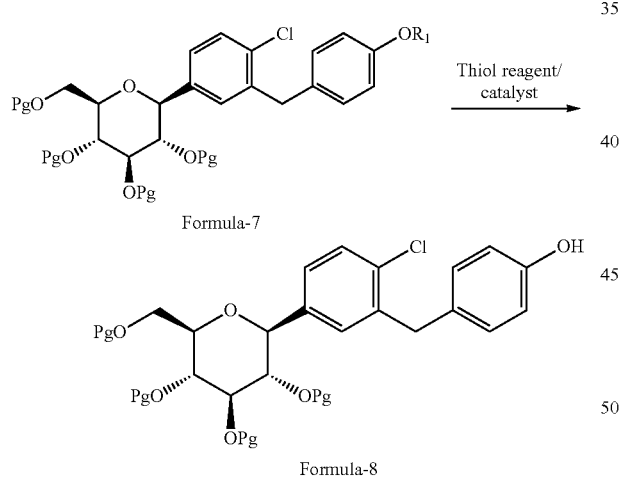

Formula-7

Thiol reagent/catalyst

Formula-8 wherein, $R_1$ is an alkyl group having $C_{1-5}$ carbon atoms, Pg is selected from —C(O)OC$_1$-C$_6$ alkyl; optionally substituted —C(O)OC$_1$-C$_6$ aryl; optionally substituted —C$_1$-C$_{12}$ aryl(C$_1$-C$_3$)alkyl; optionally substituted C$_7$-C$_{11}$ aryl carbonyl; C$_1$-C$_6$ alkanoyl; C$_1$-C$_6$ alkylsulfonyl.

7. The process of claim 6, wherein the thiol reagent is selected from the group consisting of decanethiol, dodecane thiol, cyclohexane thiol, cyclopentane thiol, cyclo butane thiol, thiophenol, methanethiol, ethanethiol, 1-propanethiol, 2-propanethiol, n-butanethiol, tert-butanthiol, furan-2-yl-methanethiol, ethandithiol, 1,2-propanedithiol, 1,3-propanedithiol, 1,3-butanedithiol, 1,4-butanedithiol.

8. The process of claim 6, wherein suitable Lewis acid catalyst is selected from the group consisting of aluminium trichloride (AlCl$_3$), aluminium tribromide (AlBr$_3$), boron trifluoride (BF$_3$), boron trichloride (BCl$_3$), titanium tetrachloride (TiCl$_4$), ferric chloride (FeCl$_3$) and zinc chloride (ZnCl$_2$).

9. The process according to claim 6, process for the preparation of compound of formula-8a,

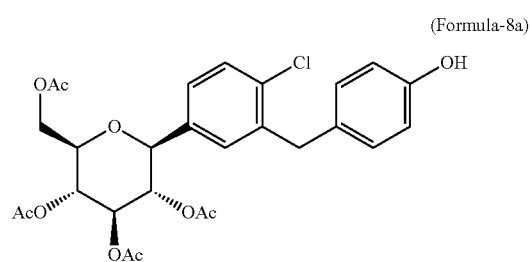 [SMILES: CC(=O)OC[C@H]1O[C@@H](c2ccc(Cl)c(Cc3ccc(O)cc3)c2)[C@H](OC(C)=O)[C@@H](OC(C)=O)[C@@H]1OC(C)=O]
(Formula-8a)

comprising reacting the compound of formula-7a with dodecanethiol/AlCl$_3$ to provide compound of formula-8a

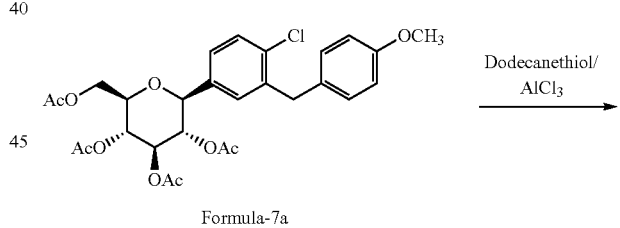

Formula-7a

Dodecanethiol/ AlCl$_3$

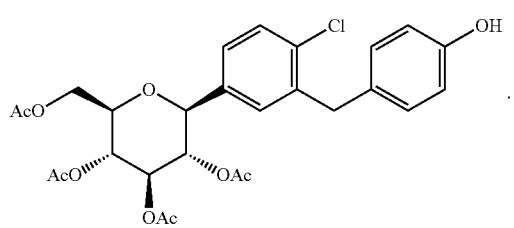

Formula-8a

10. A process for the preparation of D-glucitol, 1,5-anhydro-1-C-[4-chloro-3-[[4-[[(3S)-tetrahydro-3-furanyl]oxy]phenyl]methyl]phenyl]-, (1S), comprising wherein compound of general formula-11 is used as an intermediate

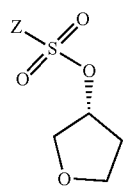

Formula-11 wherein Z is alkyl group having 1-4 carbons or aryl group selected from the group consisting of phenyl or naphthyl substituted with one or more electron withdrawing groups.

11. The process of claim 10, wherein the electron withdrawing group is selected from the group consisting of —$NO_2$, —$NH_3^+$, —$N(R_1)_3$, —CN, —CHO, —COOH, trifluoroalkyl, halogen.

12. A compound of general formula-11 of claim 10

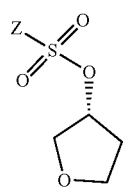

Formula-11 wherein Z is alkyl group having 1-4 carbons or aryl group selected from the group consisting of phenyl or naphthyl substituted with one or more electron withdrawing groups.

13. The compound of claim 12, wherein the compound of formula-11 is selected from the group consisting of (R)-tetrahydrofuran-3-yl 4-nitrobenzenesulfonate, (R)-tetrahydrofuran-3-yl 2-nitrobenzenesulfonate or (R)-tetrahydrofuran-3-yl methane sulfonate.

14. A process for preparing a compound according to claim 12, comprising reacting the (R)-tetrahydrofuran-3-ol with compound of general formula-12 in presence of suitable base and suitable solvent to provide compound of general formula-11

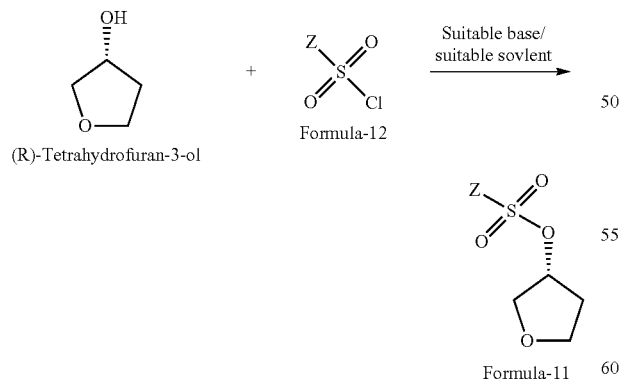

wherein, Z is alkyl group having 1-4 carbons or aryl group selected from the group consisting of phenyl or naphthyl substituted with one or more electron withdrawing groups selected from the group consisting of $NO_2$, —$NH_3^+$, —CN, —CHO, —COOH, trifluoroalkyl, halogen.

15. The process according to claim 14, wherein the suitable base is organic base or inorganic base, wherein the organic base is selected from the group consisting of dimethylaminopyridine (DMAP), triethylamine, trimethylamine, tripropylamine, diisopropylethylamine (DIPEA), pyridine or mixtures thereof; the the inorganic base is selected from the group consisting of sodium hydroxide, sodium carbonate, sodium bicarbonate, potassium hydroxide, potassium carbonate, potassium bicarbonate, sodium hydride.

16. The process according to claim 14, wherein the suitable solvent is selected from the group consisting of methylene chloride, methanol, ethanol, isopropanol, n-butanol, isobutanol, ethyl acetate, methyl acetate, propyl acetate, acetonitrile, dimethyl formamide, dimethylacetamide, diethyl ether, methyl tert-butyl ether, and tetrahydrofuran.

17. The process of according to claim 14, comprising reacting (R)-tetrahydrofuran-3-ol with 4-nitrobenzene-1-sulfonyl chloride in presence of dimethylaminopyridine, triethylamine in methylene chloride

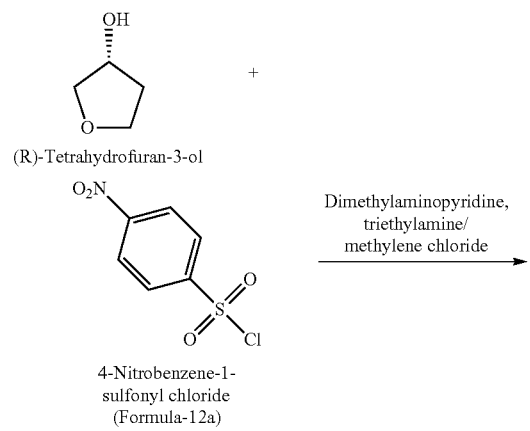

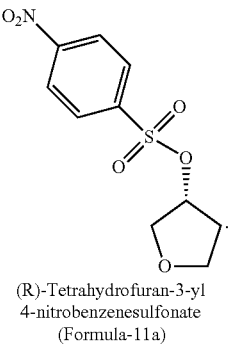

* * * * *